(12) United States Patent
Weilbacher et al.

(10) Patent No.: US 9,358,348 B2
(45) Date of Patent: Jun. 7, 2016

(54) SAFETY SHIELD FOR MEDICAL NEEDLES

(75) Inventors: Eugene E. Weilbacher, Chesterfield, MO (US); Casey Chebator, Weymouth, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/237,722

(22) Filed: Sep. 25, 2008

(65) Prior Publication Data
US 2009/0062744 A1 Mar. 5, 2009

Related U.S. Application Data

(63) Continuation-in-part of application No. 11/452,643, filed on Jun. 14, 2006, now Pat. No. 8,551,051.

(60) Provisional application No. 60/995,615, filed on Sep. 27, 2007.

(51) Int. Cl.
*A61M 5/32* (2006.01)
*A61M 5/158* (2006.01)
(Continued)

(52) U.S. Cl.
CPC ............. *A61M 5/3273* (2013.01); *A61M 5/158* (2013.01); *A61M 5/3243* (2013.01); *A61M 5/3271* (2013.01); *A61M 5/3134* (2013.01); *A61M 5/3137* (2013.01); *A61M 5/3202* (2013.01); *A61M 5/329* (2013.01); *A61M 5/3287* (2013.01);
(Continued)

(58) Field of Classification Search
CPC ... A61M 5/322; A61M 5/3234; A61M 5/508; A61M 5/3271; A61M 5/3243
USPC .................................................. 604/110, 198
See application file for complete search history.

(56) References Cited

U.S. PATENT DOCUMENTS 2,559,474 A    7/1951   Son
2,739,591 A    3/1956   Yochem
(Continued)

FOREIGN PATENT DOCUMENTS

EP    0 680 767 A1    11/1995
WO    WO 95/28979 A1    11/1995
(Continued)

OTHER PUBLICATIONS

European Search Report, EP Application No. 06 25 3097, Sep. 28, 2006.
(Continued)

*Primary Examiner* — Kami A Bosworth
*Assistant Examiner* — Matthew A Engel

(57) ABSTRACT

A safety needle apparatus is provided. The safety needle apparatus includes a needle assembly including a needle mount and a needle cannula. The needle cannula defines a lumen and has a sharpened distal tip. The needle mount supports the proximal end of the needle cannula and is adapted to engage an intravenous line. The safety apparatus includes a shield positioned about the needle cannula. The needle cannula is movable in relation to the shield. The apparatus also includes a lock insert supported on the needle cannula and a locking member extending from an internal surface of the shield, wherein the locking insert and the locking member are configured to prevent movement of the needle cannula. A platform including a base member, which is configured to support the needle cannula at a substantially orthogonal orientation to the plane of a top surface of the platform and supports the shield, is included.

11 Claims, 25 Drawing Sheets

(51) Int. Cl.
  *A61M 5/31* (2006.01)
  *A61M 5/34* (2006.01)
  *A61M 5/50* (2006.01)
  *A61M 39/02* (2006.01)

(52) U.S. Cl.
  CPC .............. *A61M 5/349* (2013.01); *A61M 5/5086* (2013.01); *A61M 39/0208* (2013.01); *A61M 2005/1581* (2013.01); *A61M 2005/1585* (2013.01); *A61M 2005/3247* (2013.01); *A61M 2005/3252* (2013.01)

(56) References Cited

U.S. PATENT DOCUMENTS

| | | | |
|---|---|---|---|
| 3,797,490 A * | 3/1974 | Hurschman | A61M 5/28 604/196 |
| 3,820,542 A * | 6/1974 | Hurschman | A61M 5/28 604/196 |
| 4,160,450 A | 7/1979 | Doherty | |
| 4,194,505 A * | 3/1980 | Schmitz | A61M 5/2033 604/138 |
| 4,573,976 A | 3/1986 | Sampson et al. | |
| 4,725,267 A | 2/1988 | Vaillancourt | |
| 4,738,663 A | 4/1988 | Bogan | |
| 4,747,831 A | 5/1988 | Kulli | |
| 4,762,516 A | 8/1988 | Luther et al. | |
| 4,795,432 A | 1/1989 | Karczmer | |
| 4,900,307 A | 2/1990 | Kulli | |
| 4,909,793 A | 3/1990 | Vining et al. | |
| 4,955,866 A | 9/1990 | Corey | |
| 4,978,344 A | 12/1990 | Dombrowski et al. | |
| 4,986,811 A * | 1/1991 | Thead | A61M 5/3205 206/366 |
| 4,994,041 A | 2/1991 | Dombrowski et al. | |
| 4,994,046 A | 2/1991 | Wesson et al. | |
| 5,026,356 A | 6/1991 | Smith | |
| 5,086,922 A * | 2/1992 | Sagstetter | A61M 5/3205 206/366 |
| 5,215,534 A | 6/1993 | De Harde et al. | |
| 5,300,030 A * | 4/1994 | Crossman | A61M 5/2033 604/134 |
| 5,312,347 A * | 5/1994 | Osborne | A61M 5/002 604/110 |
| 5,338,311 A | 8/1994 | Mahurkar | |
| 5,348,544 A | 9/1994 | Sweeney et al. | |
| 5,423,766 A | 6/1995 | DiCesare | |
| 5,466,223 A | 11/1995 | Bressler et al. | |
| 5,496,274 A * | 3/1996 | Graves | A61M 39/1011 604/192 |
| 5,501,675 A | 3/1996 | Erskine | |
| 5,514,100 A | 5/1996 | Mahurkar | |
| 5,527,287 A * | 6/1996 | Miskinyar | A61M 5/14248 604/135 |
| 5,584,810 A | 12/1996 | Brimhall | |
| 5,584,818 A | 12/1996 | Morrison | |
| 5,599,310 A | 2/1997 | Bogert | |
| 5,672,161 A | 9/1997 | Allen et al. | |
| 5,685,862 A | 11/1997 | Mahurkar | |
| 5,690,619 A | 11/1997 | Erskine | |
| 5,702,369 A | 12/1997 | Mercereau | |
| 5,738,665 A | 4/1998 | Caizza et al. | |
| 5,865,806 A | 2/1999 | Howell | |
| 5,873,462 A * | 2/1999 | Nguyen | A61M 5/002 206/366 |
| 5,879,337 A | 3/1999 | Kuracina et al. | |
| 5,879,338 A | 3/1999 | Mahurkar | |
| 5,891,105 A | 4/1999 | Mahurkar | |
| 5,893,845 A | 4/1999 | Newby et al. | |
| 5,910,130 A | 6/1999 | Caizza et al. | |
| 5,911,705 A | 6/1999 | Howell | |
| 5,957,887 A | 9/1999 | Osterlind et al. | |
| 5,976,111 A * | 11/1999 | Hart | A61M 5/326 128/919 |
| 6,001,080 A | 12/1999 | Kuracina et al. | |
| 6,086,562 A * | 7/2000 | Jacobsen | A61M 5/20 604/131 |
| 6,117,112 A | 9/2000 | Mahurkar | |
| 6,132,401 A | 10/2000 | Van Der Meyden et al. | |
| 6,183,445 B1 | 2/2001 | Lund et al. | |
| 6,280,401 B1 | 8/2001 | Mahurkar | |
| 6,322,537 B1 | 11/2001 | Chang | |
| 6,409,701 B1 | 6/2002 | Cohn et al. | |
| 6,569,123 B2 * | 5/2003 | Alchas | A61M 5/46 604/192 |
| 6,582,402 B1 | 6/2003 | Erskine | |
| 6,638,254 B2 | 10/2003 | Nakagami | |
| 6,761,706 B2 | 7/2004 | Vaillancourt | |
| 6,767,336 B1 | 7/2004 | Kaplan | |
| 6,986,760 B2 * | 1/2006 | Giambattista | A61M 5/002 604/110 |
| 7,407,493 B2 * | 8/2008 | Cane' | A61M 5/158 206/365 |
| 7,540,858 B2 * | 6/2009 | DiBiasi | A61M 5/326 604/192 |
| 7,670,314 B2 * | 3/2010 | Wall | A61M 5/19 604/135 |
| 8,152,771 B2 * | 4/2012 | Mogensen | A61M 5/158 604/157 |
| 8,162,892 B2 * | 4/2012 | Mogensen | A61M 5/158 604/157 |
| 8,172,805 B2 * | 5/2012 | Mogensen | A61M 5/158 604/157 |
| 2002/0099338 A1 | 7/2002 | Young | |
| 2002/0133122 A1 * | 9/2002 | Giambattista | A61M 5/3202 604/198 |
| 2003/0187395 A1 * | 10/2003 | Gabel | A61M 5/14248 604/134 |
| 2004/0116847 A1 * | 6/2004 | Wall | A61K 9/0019 604/93.01 |
| 2004/0116853 A1 | 6/2004 | Halseth et al. | |
| 2004/0204687 A1 * | 10/2004 | Mogensen | A61M 5/158 604/181 |
| 2005/0038392 A1 * | 2/2005 | DeSalvo | A61M 5/3243 604/198 |
| 2005/0043687 A1 * | 2/2005 | Mogensen | A61M 5/158 604/181 |
| 2005/0080378 A1 | 4/2005 | Cindrich | |
| 2011/0301542 A1 * | 12/2011 | Schwartz | A61M 5/1626 604/164.08 |

FOREIGN PATENT DOCUMENTS

| | | |
|---|---|---|
| WO | 0145776 A1 | 6/2001 |
| WO | WO 02/45786 A2 | 6/2002 |
| WO | WO 02/083213 A1 | 10/2002 |

OTHER PUBLICATIONS

European Search Report corresponding to European Application No. 08166654.7, dated Apr. 6, 2010 (7 Pages).

Patent Examination Report No. 2 for AU Application No. 2009222435 dated Nov. 1, 2013, 3 pages, Woden, Australia.

Office Action dated Feb. 8, 2016 in related U.S. Appl. No. 14/013,050, 8 pages.

* cited by examiner

SAFETY SHIELD FOR MEDICAL NEEDLES

CROSS-REFERENCE TO RELATED APPLICATION

This application claims the benefit of and priority to Provisional Application 60/995,615 filed on Sep. 27, 2007. This application is also a continuation-in-part of U.S. patent application Ser. No. 11/452,643 filed on Jun. 14, 2006 now U.S. Pat. No. 8,551,051. The contents of each of these applications are hereby incorporated by reference in their entirety.

BACKGROUND

1. Technical Field

The present disclosure generally relates to safety shields for medical needles, and more particularly, to manually activated safety shields that employ structure for positioning and locking a shield.

2. Description of the Related Art

Problems associated with inadvertent needle sticks are well known in the art of blood sampling, percutaneous medication injection, and other medical procedures involving use of medical needles. Significant attention has been focused on needle stick problems due to the contemporary sensitivity of exposure to HIV, hepatitis, and other serious blood-borne pathogens.

Procedures for removing a needle from a patient commonly require a clinician to use one hand to place pressure at the wound site where a needle is being withdrawn, while removing the needle device with the other hand. It is also common practice for a clinician to give higher priority to care for the wound than is given to disposal of the needle. In the case of typical needle devices without safety shields, such priority either requires the convenience of an available sharps container within reach or another means for safe disposal, without leaving the patient's side. Thus, the difficulty in providing adequate care while following safety procedures is often compounded by the patient's physical condition and mental state, such as in burn units and psychiatric wards. Under such conditions, proper disposal of a used needle, while caring for a patient, is a technological challenge to the state of the art.

The widespread knowledge and history associated with needle care and disposal problems have resulted in numerous devices for minimizing accidental needle sticks. Some devices utilize a separate sheath or cap mounted over the needle after use. Other known devices employ sheaths that are spring activated or pivoting. Drawbacks of current devices include high manufacturing cost due to complexity and the number of parts.

Therefore, it would be desirable to provide a more adequate and reliable safety apparatus having a medical needle shield that employs structure for positioning and locking a shield to minimize hazardous exposure to a needle. It would be highly desirable if the medical needle shield is easily and efficiently assembled and manufactured.

SUMMARY

A safety needle apparatus is provided. The safety needle apparatus includes a needle assembly including a needle mount and a needle cannula. The needle cannula defines a lumen and has a sharpened distal tip. The needle mount supports the proximal end of the needle cannula and is adapted to engage an intravenous line. The safety needle apparatus further includes a shield positioned about the needle cannula. The needle cannula is movable in relation to the shield from an advanced position in which the distal tip of the needle cannula extends from the distal end of the shield to a retracted position in which the distal tip of the needle cannula is positioned within the shield. The safety needle apparatus also includes a platform which supports the shield. The platform includes a base member which is configured to support the needle cannula at a substantially orthogonal orientation to the plane defined by a top surface of the platform.

In one embodiment, a lock insert is supported on the needle cannula and a locking member extends from an internal surface of the shield. The locking insert and the locking member are configured to prevent movement of the needle cannula to the advanced position after the needle cannula has been moved to the retracted position. In one embodiment, the lock insert includes one or more resilient projection members, which extend radially outwardly in their normal configuration. The locking member includes one or more protrusions, which have a generally annular shape or configuration and extend inwardly from an inner surface of the shield. Alternatively, the locking member may include one or more grooves located on the inner surface of the shield.

In another embodiment, a lock insert is supported on the internal surface of the shield and a locking member extends outwardly from an outer surface of the needle cannula. The lock insert includes one or more protrusions that are movable radially outward. In one embodiment, the locking member is an annular tab which extends in a generally orthogonal direction from an outer surface of the needle cannula. Alternatively, the locking member may be in the form of an annular groove disposed on the outer surface of the needle cannula.

BRIEF DESCRIPTION OF THE DRAWINGS

The foregoing and other features and advantages of the present disclosure will be more fully understood from the following detailed description of the embodiments, taken in conjunction with the accompanying drawings in which.

DETAILED DESCRIPTION OF THE EMBODIMENTS

Figure 1:
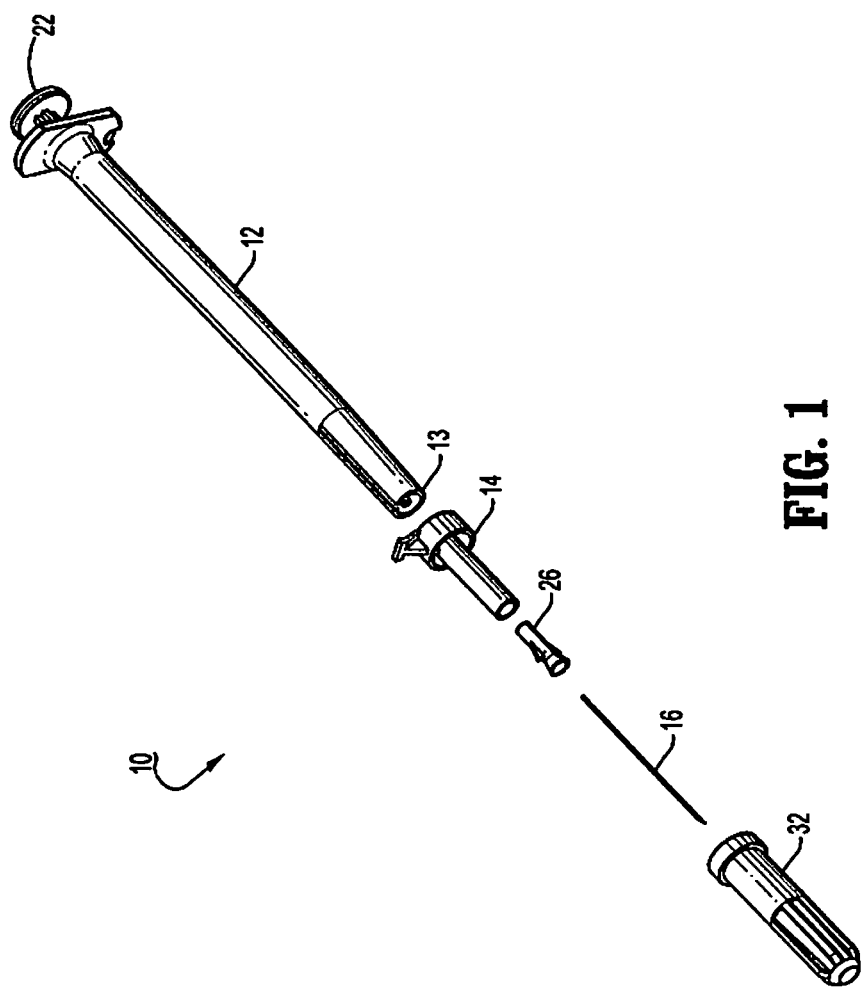
FIG. 1 is an exploded perspective view of a safety apparatus in accordance with the principles of the present disclosure.
Figure 2:
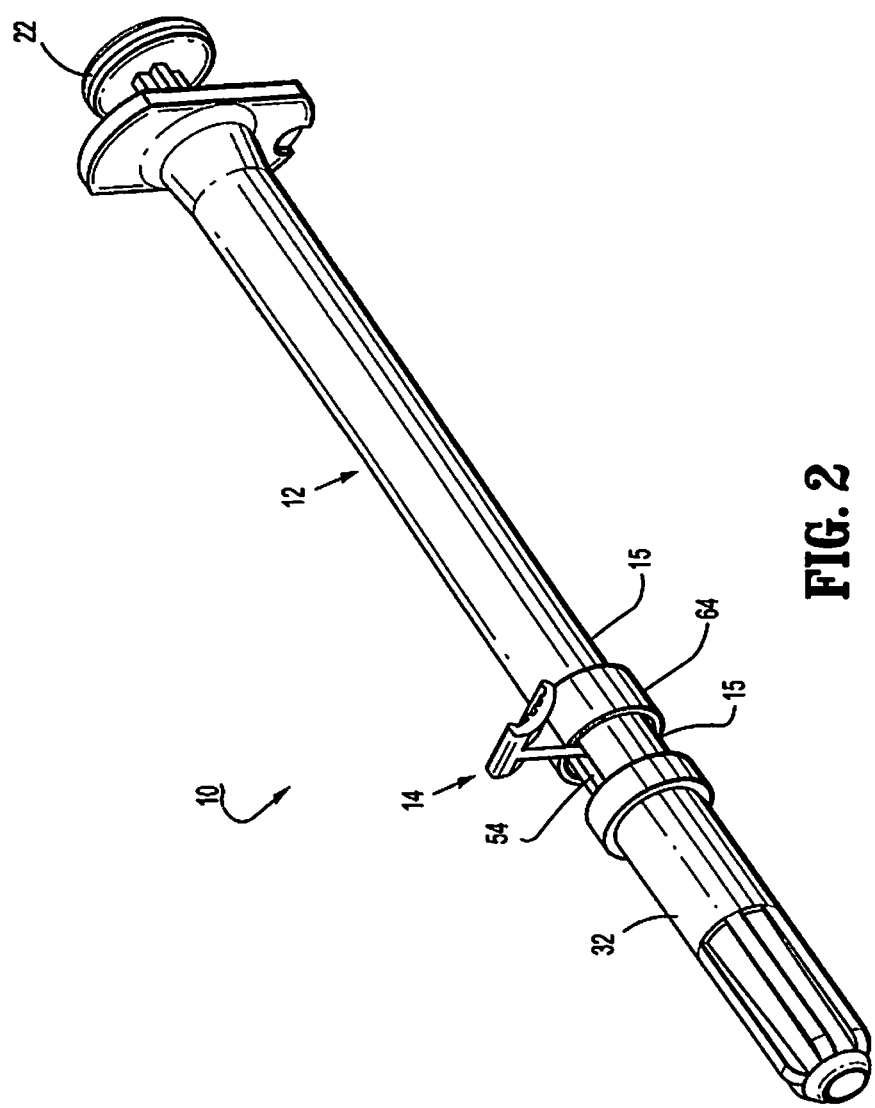
FIG. 2 is a perspective view of the apparatus shown in FIG. 1.

The embodiments of the safety apparatus and the methods of operation disclosed herein are discussed in terms of safety shields for medical needles for infusion of medication and nutrition fluids (via, for example, subcutaneous, intradermal, intravenous and/or intramuscular), and fluid collection, and more particularly, in terms of manually actuated safety shields that employ structure for positioning and locking a shield to minimize hazardous exposure to the needle cannula, for example, through an inadvertent needle stick. It is contemplated that the needle cannula may be shielded during use including storage, transport, fluid infusion, and/or collection, subsequent thereto, etc. It is envisioned that the present disclosure, however, finds application to a wide variety of cannula needles, including small needle applications and devices for the infusion of preventive medications, medicaments, and therapeutics to a subject. It is also envisioned that the present disclosure may be employed for collection of body fluids including those employed during procedures relating to phlebotomy, digestive, intestinal, urinary, and veterinary and the like. It is also contemplated that the safety apparatus may be utilized with other medical needle applications including feeding devices, phlebotomy devices, catheters, catheter introducers, guide wire introducers, spinal and epidural, biopsy, aphaeresis, dialysis, blood donor, Veress needles, Huber needles, and the like.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the safety apparatus. According to the present disclosure, the term "clinician" refers to an individual administering an infusion, performing fluid collection, installing or removing a needle cannula from a safety apparatus and may include support personnel.

The following discussion includes a description of the safety apparatus, in accordance with the present disclosure. Reference will now be made in detail to the embodiments of the disclosure, which are illustrated in the accompanying figures.

Turning now to the figures, wherein like components are designated by like reference numerals throughout the several views. Referring to FIGS. 1-10, there is illustrated a safety apparatus, such as, for example, a needle syringe or syringe 10. The syringe 10, as shown in FIGS. 1-5, includes a first tubular member, such as, for example, a syringe barrel or barrel 12 having a needle cannula or needle 16 mounted therewith via a needle mount 11. An open beveled portion 23 is disposed at a distal end of needle cannula 16. Needle cannula 16 is adhesively mounted to syringe barrel 12 at needle mount 11. Needle mount 11 includes nipple portion 19 (FIG. 3) for holding adhesive. Needle cannula 16 penetrates needle mount 11 generally between a depth of 0.010-0.020 inches. The adhesive is used to secure needle cannula 16 to needle mount 11. The adhesive forms a meniscus at nipple portion 19 and is interiorly displaced along the needle cannula shaft and the needle mount 11 about one-half of the needle penetration depth. A second tubular member, such as, for example, a tubular shield 14, is mounted with the barrel 12 and is movable from a retracted position (FIG. 3) whereby the needle 16 is exposed, to an extended position (FIGS. 4 and 5) whereby the needle 16 is covered. A lock, such as, for example, a tubular lock insert 26 is mounted with the barrel 12 such that the shield 14 is slidably movable along an outer surface 28 of the lock insert 26. The lock insert 26 includes arms or tangs 30 that are movable radially outward to fix the shield 14 in the extended position. It is contemplated that one or more tangs 30 may be employed with lock insert 26.

A removable sheath 32 (FIGS. 1 and 2) covers the needle 16 during transport and prior to use. The sheath 32 is ribbed to inhibit rolling when the syringe 10 is placed on a surface. Sheath 32 may include other structure configured to inhibit rolling such as projections, pads and the like. The sheath 32 is removably coupled to the syringe barrel 12. Sheath 32 is not in contact with shield 14 so as to inhibit inadvertent actuation of the syringe 10 when sheath member 32 is pulled off prior to use. Sheath 32 may be heat staked to syringe barrel 12 as a tamper evident feature as is known in the art.

Figure 3:
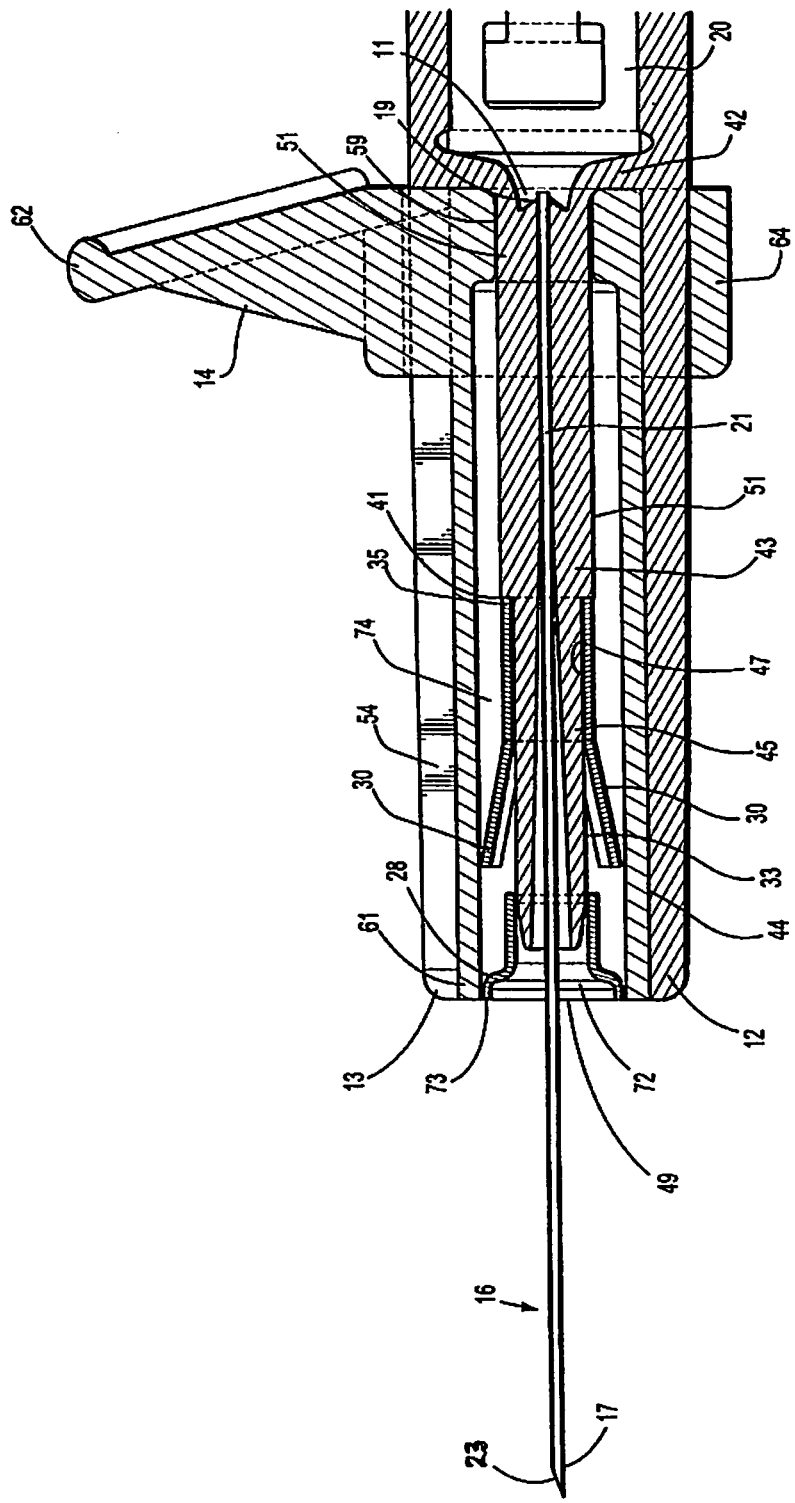
FIG. 3 is a cross-sectional side view of a distal portion of the apparatus shown in FIG. 1, in a ready-to-use position.
Figure 6:
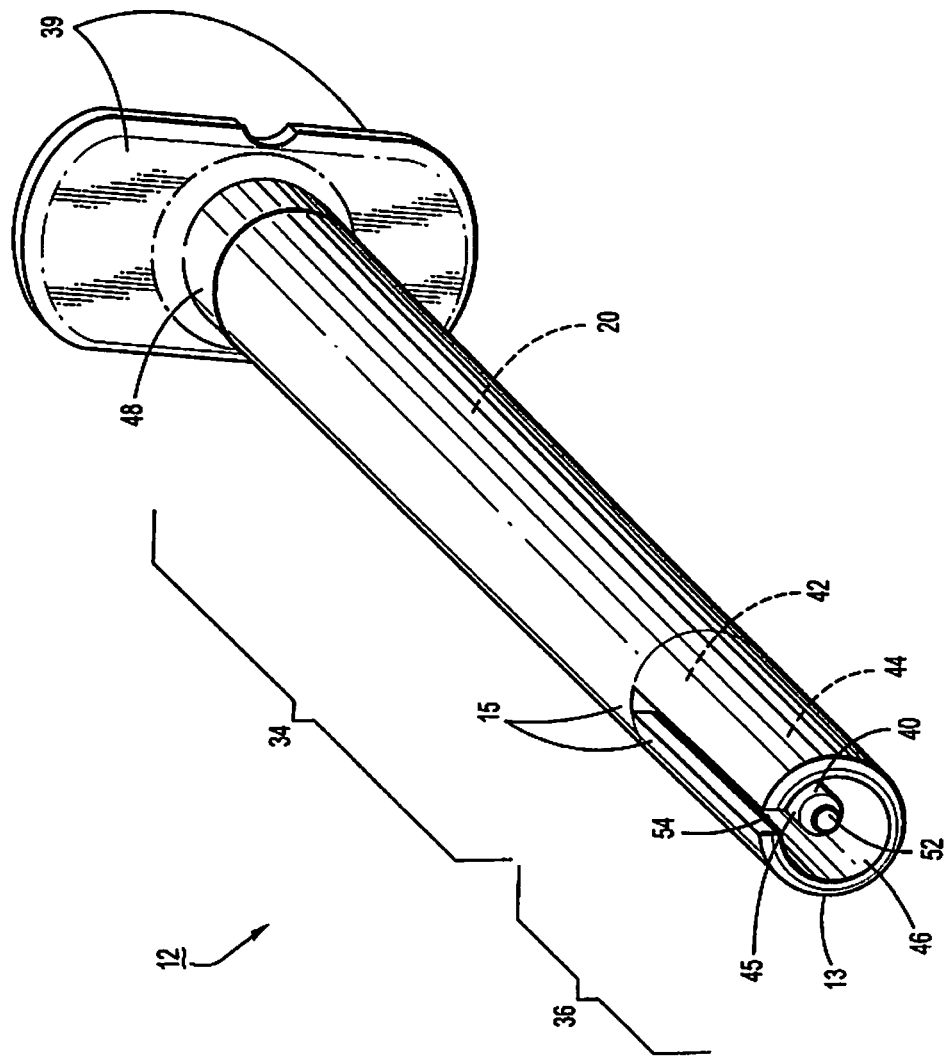
FIG. 6 is a perspective view of a barrel of the apparatus shown in FIG. 1.

A proximal portion 34 of the barrel 12, as shown in FIG. 6, defines a plunger cavity 20 configured for receipt of a plunger 22 (FIG. 1). Finger flanges 39 are disposed adjacent a proximal end 48 of the barrel 12 to facilitate manipulation of the syringe 10. A distal portion 36 of the barrel 12 includes a post 40 on which the shield 14 is slidably mounted and lock insert 26 is fixedly mounted. As shown in FIG. 3, the post 40 has a distal end 45 with an outer annular surface 47 and a proximal end 43 with an outer annular surface 51. The proximal end 43 has a slightly greater diameter than that of the distal end 45. A circumferential ridge 41 is defined by the juncture of the outer annular surface 47 and the outer annular surface 51.

Figure 4:
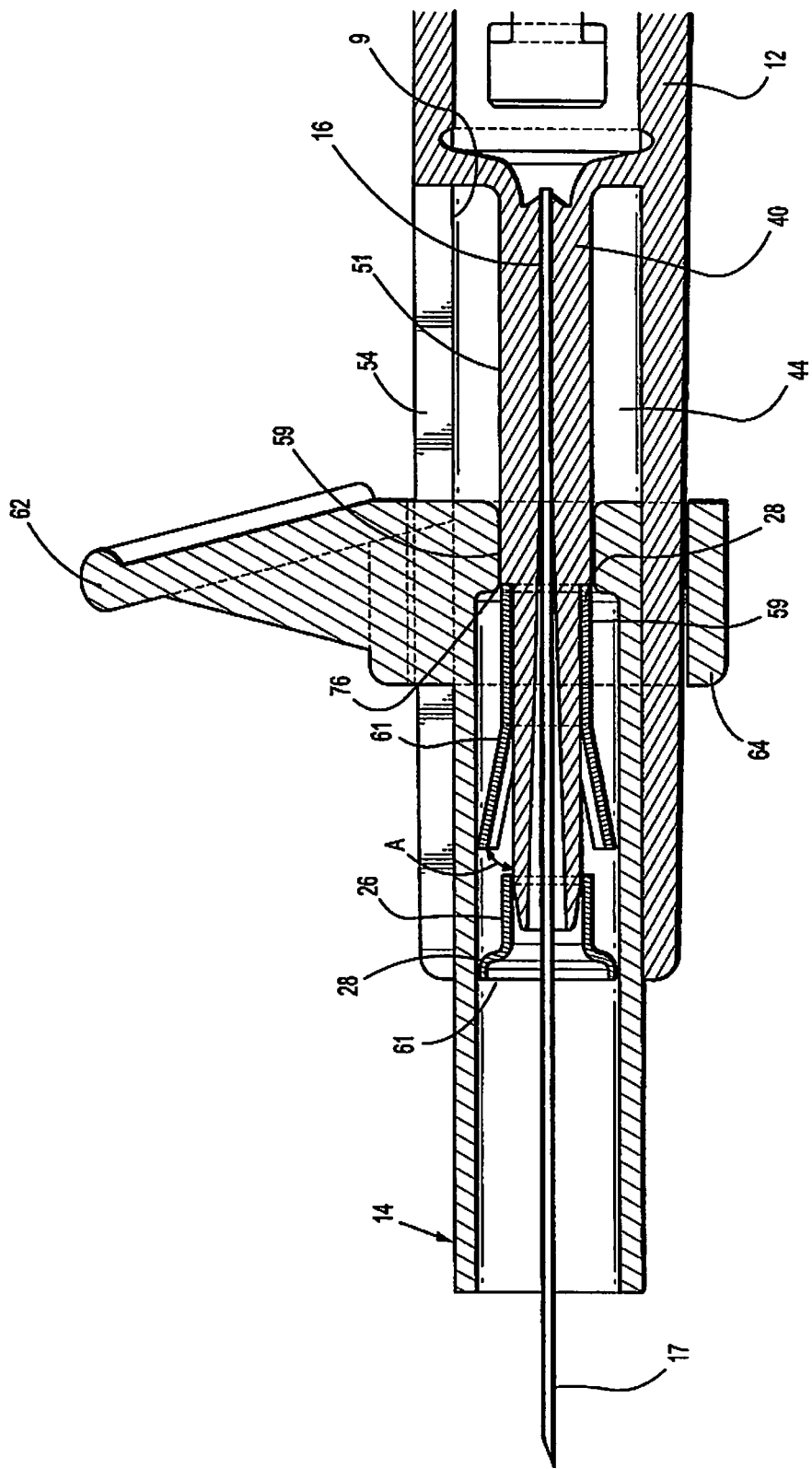
FIG. 4 is a cutaway cross-sectional side view of the distal portion of the apparatus shown in FIG. 1, in an extended position.
Figure 7:
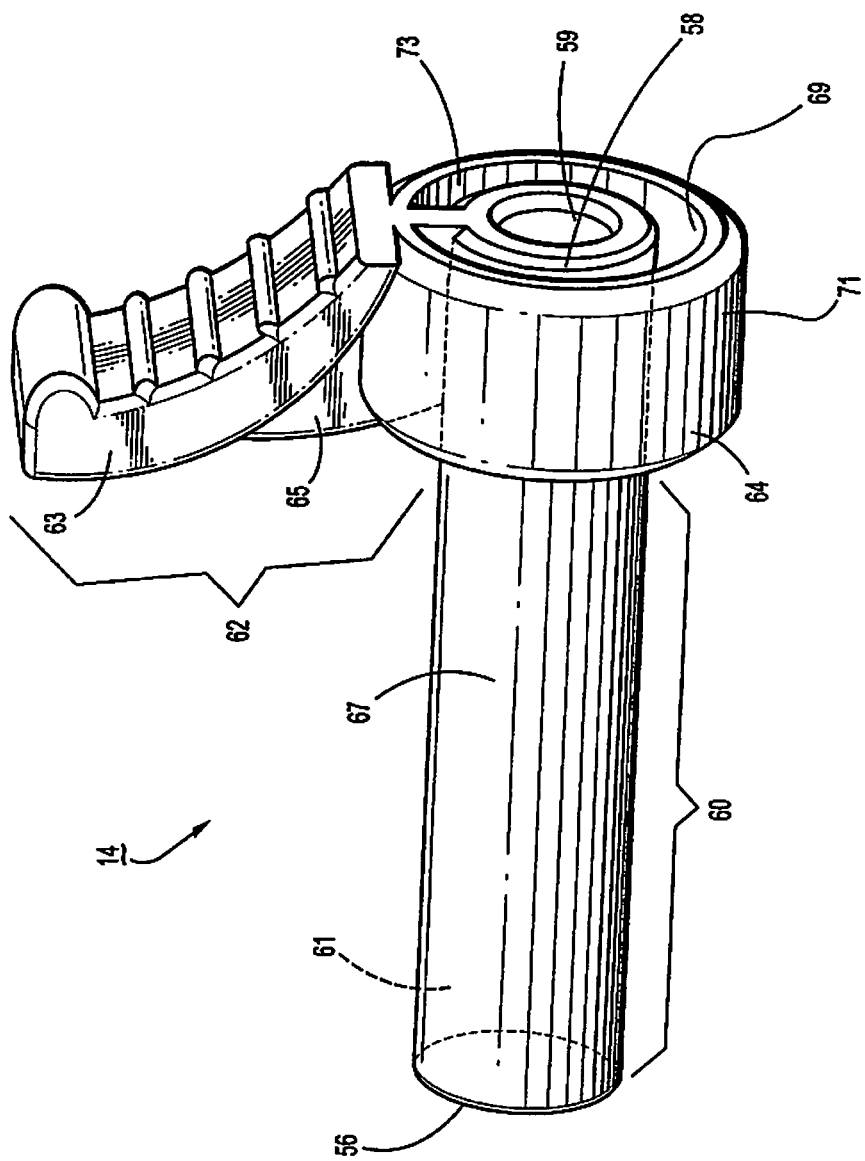
FIG. 7 is a perspective view of a shield of the apparatus shown in FIG. 1.

Barrel 12 further includes a channel such as, for example, race 46. The race 46 and post 40 define a cavity 44 configured for slidable movement of the shield 14 (FIG. 7). The race 46 and post 40 guide and support the shield 14 during travel in the cavity 44 and inhibit free play between the components. The cavity 44, as shown in FIGS. 3 and 4, has a tubular configuration and is bound longitudinally by a closed proximal end 42 and an open distal end 49. Cavity 44 has a circular cross section and is bound cross sectionally by the inner circumference 9 of the barrel 12 and the outer annular surfaces 47, 51 of the post 40. The cavity 44 may have alternative geometries to facilitate movement of the shield 14, for example, the cavity 44 may have an oval, tubular, hollow, or other polygonal cross section. The cavity 44 may also be concentric with shield 14. A longitudinal slot 54 extends from a distal end 13 of the barrel 12 along an outer wall 15 thereof. The slot 54 is configured to guide movement of the shield 14, as explained in greater detail below. The post 40 defines a needle cavity 52 that engages an outer surface of the needle 16 for support thereof. A proximal end (not shown) of the needle 16 extends into the plunger cavity 20 for fluid communication therewith. In addition, plunger cavity 20 is in fluid communication with beveled portion 23, thereby permitting fluid stored in plunger cavity 20 to be communicated through needle cannula 16 and beyond its distal end.

The shield 14, as shown in FIG. 7, is configured for telescopic mounting within the cavity 44 of the syringe barrel 12. It is contemplated that the shield 14 may include a tube portion 60 configured for covering the needle 16 and having an inner surface 61. A proximal end 58 of the tube 60 has a narrowed inner surface 59. A circumferential ridge 76 (FIG. 4) is defined by the juncture of the inner surface 61 and the narrowed inner surface 59. An actuator 62 is disposed with the tube 60 for causing slidable movement of the shield 14. The actuator 62 includes a neck 65 that extends radially from the proximal end 58 of the tube 60. A ribbed finger pad 63 is disposed with the neck 65.

The shield 14 includes a stability member, such as, for example, a stability ring 64 to provide additional stability during axial movement of the shield 14 with respect to the barrel 12 of the syringe 10. The stability ring 64 adds structural integrity to keep the shield 14 firmly in place when it is locked in the fully extended position. Ring 64 surrounds the tube 60 near the proximal end 58 such that a gap 73 exists between the shield's outer wall 67 and the ring 64. The ring 64 intersects the actuator 62 and includes an inner surface 69 and an outer surface 71. The stability member 64 may have alternate geometries configured to provide stability and/or structural integrity.

Figure 8A:
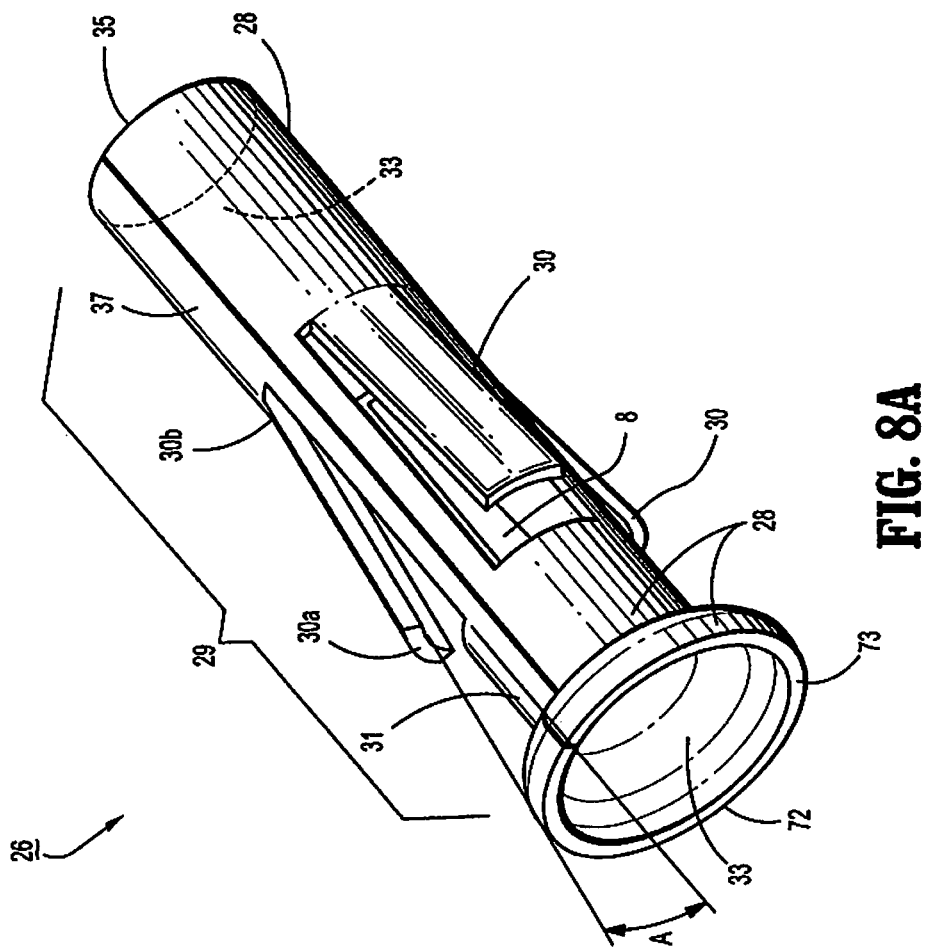
FIG. 8A is a perspective view of an insert of the apparatus shown in FIG. 1.

The lock insert 26, as shown in FIG. 8A, is configured for mounting on the post 40. As will be later explained in greater detail, the lock insert 26 retains the shield 14 in a "ready-to-use" position and inhibits distal sliding of the shield 14. The lock insert 26 also inhibits the shield 14 from traveling proximally from a fully shielded position. The lock insert 26 has annular inner surfaces 33 and annular outer surfaces 28, and includes a tubular lock sleeve 29 having a distal end 31 and a proximal end 37. A stop member, such as, for example, a protruding rim or flange 72 is disposed at the distal end 31 and includes a circumferential edge 73. The proximal end 37 includes a circumferential edge 35.

The lock insert 26 includes a projection member, such as for example, a tang 30 that is movable radially outward to fix the shield 14 in the extended position. One or a plurality of tangs 30 may be employed. The tang 30 is disposed circumferentially about the outer surface 28 of the lock insert 26 intermediate the distal and proximal ends 31, 37 of the sleeve 29. Tang 30 is cantilevered from sleeve 29 through cutout 8 in the surface 28. The tang 30 is pivotable from its proximate edge 30b. Tang 30 is biased for radially outward movement such that its distal end 30a tends to extend above the surface 28 to define an angle A therewith. When compressed, the tang 30 pivots into substantial alignment with the surface 28. The lock insert 26 may include other structure configured to lock the shield 14 such as, stops, protuberances and the like. Operation of the lock insert 26 is described below in more detail.

Figure 8B:
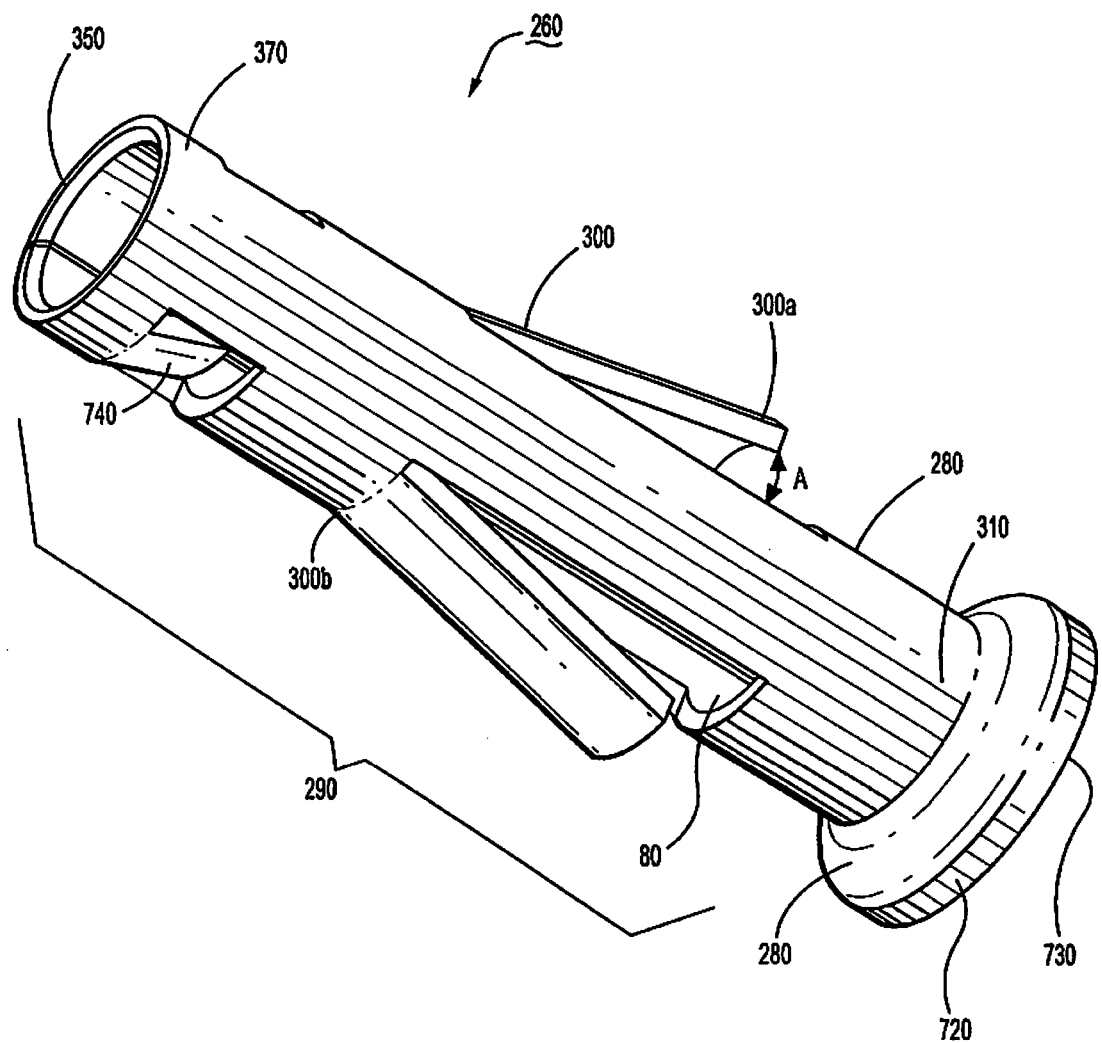
FIG. 8B is a perspective view of an alternate insert of the apparatus in accordance with the principles of the present disclosure.
Figure 8C:
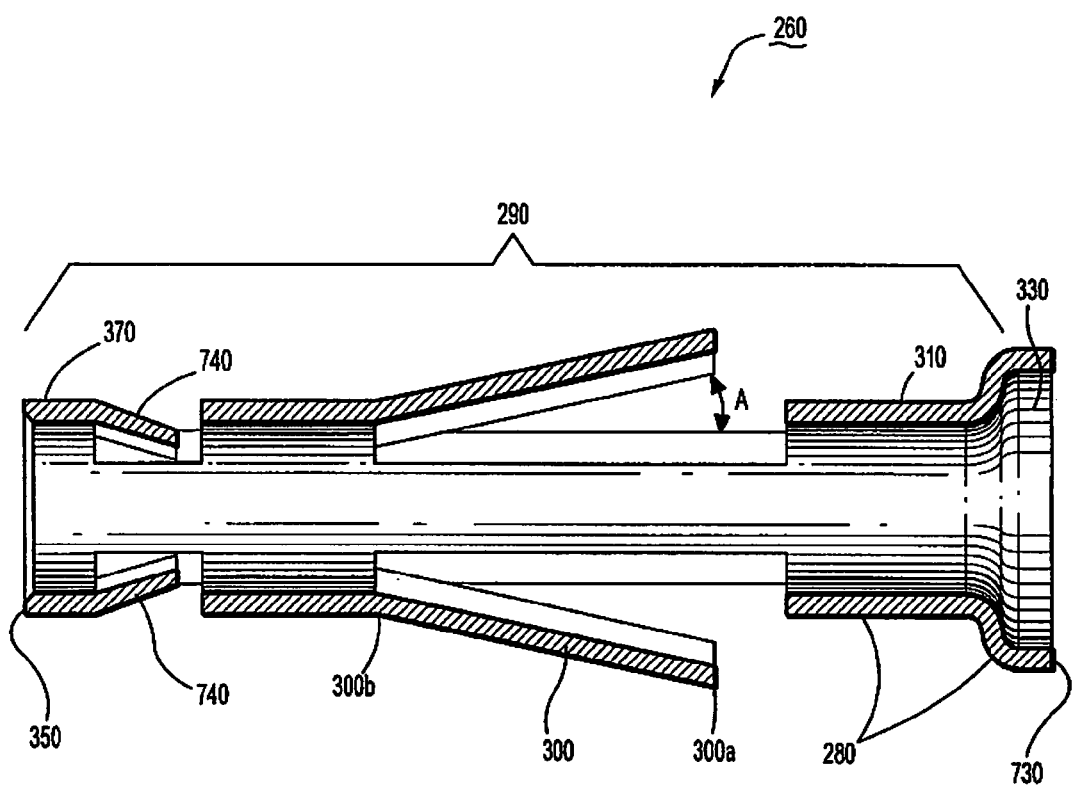
FIG. 8C is a cross-sectional view of the insert shown in FIG. 8B.

With reference to FIGS. 8B and 8C, where like reference numerals are used to designate like elements for the sake of simplicity of explanation, there is disclosed an alternative embodiment of lock insert 26. Lock insert 260 is configured for mounting on post 40 and is designed to retain the shield 14 (FIG. 4) in a "ready-to-use" position and inhibits distal sliding of the shield 14. The lock insert 260 also inhibits the shield 14 from traveling proximally from a fully shielded position. The lock insert 260 has inner annular surfaces 330 and outer annular surfaces 280 and includes a tubular lock sleeve 290 having a distal end 310 and a proximal end 370. A flange 720 is disposed at the distal end 310 and includes a circumferential edge 730. The proximal end 370 includes a circumferential edge 350.

The lock insert 260 includes a tang 300 that is movable radially outward to fix the shield 14 in the extended position. One or a plurality of tangs 300 may be employed. The tang 300 is disposed circumferentially about the outer surface 280 of the lock insert 260 intermediate the distal 310 and proximal 370 ends of the sleeve 290. Tang 300 is cantilevered from sleeve 290 through cutout 80 in the surface 280. The tang 300 is pivotable from its proximate edge 300b. Tang 300 is biased for radially outward movement such that its distal end 300a tends to extend above the surface 280 to define an angle A therewith. When compressed, the tang 300 pivots into substantial alignment with the surface 280. The lock insert 260 may include additional structure configured to lock the shield 14 such as projection member 740 that is disposed circumferentially about the outer surface 280 of the lock insert 260 and is biased radially inward to secure or fix the insert 260 to the outer surface 47 of the post 40 (FIG. 3). One or a plurality of projection members 740 maybe employed with insert 260.

It is contemplated that the lock inserts 26, 226 (discussed in detail hereinbelow), and 260 may be fabricated from metal or other durable material suitable for medical applications, such as, for example, stainless steel. More particularly, the lock inserts may be formed, for example, by a process known as progressive die forming wherein a die component combines a number of forming and stamping functions such as blanking, forming, flange forming, punching, and trimming into a single die. The metal blank that will ultimately form the lock inserts is fed into the die. Each time the die cycles, a stamping operation is made on the metal blank material and it is automatically advanced to the next position. Each station within the progressive die process serves to progressively form, the final lock inserts. Finally, the completed lock inserts 26, 226, and 260 are ejected from the end of the progressive die once all the operations have been completed.

The components of the safety apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

The lock insert 26 is securely mounted, as shown in FIG. 3, on the distal end 45 of the post 40 via interference between an inner surface 33 of the lock sleeve 29 and an outer surface 47 of the post 40. To further secure the lock insert 26 on the post 40, the circumferential edge 35 of the lock insert 26 abuts the circumferential ridge 41 of the post 40. In this regard, the outer surface 28 of the lock sleeve 29 is substantially aligned with the outer surface 51 along the proximal end 43 of the post 40. A distal edge 73 of the flange 72 is substantially aligned with the distal end 13 of the barrel 12. The tangs 30 extend at an angle from the outer surface 28 of the lock sleeve 29, as described above.

The assembly of the syringe 10 can be performed sequentially. For example, shield 14 may be inserted into the distal end of syringe barrel 12 followed by lock insert 26 and then finally assembly of needle cannula 16 to syringe barrel 12. The needle cannula 16 can be attached to syringe barrel 12 at any point during the assembly procedure.

The operation of the syringe 10 during a medical procedure will now be described. Initially, proper preparation and sterilization of the syringe 10 is performed (not shown), and the sheath 32 is removed. The shield 14, as shown in FIG. 3, is mounted telescopically on the post 40 in the "ready-to-use" (i.e. retracted) position whereby the distal portion 17 of the needle 16 is exposed. The narrowed end 58 of the shield 14 is adjacent the proximal wall 42 of the cavity 44 and the narrowed inner surface 59 of the shield 14 is contiguous with the outer surface 51 of the post 40. The distal inner surface 61 of the shield 14 is proximate the outer surface 28 of the lock flange 72.

There is a gap 74 between the inner surface 61 of the shield 14 and the outer annular surfaces 47, 51 of the post 40. The tang 30 is biased for radially outward movement and thus extends in the gap 74 such that distal end 30a is proximate the inner surface 61. The stability ring 64 associated with the shield 14 is disposed circumferentially about the outside wall 15 of the barrel 12. The actuator 62 of the shield 14 extends through the slot 54. The lock insert 26 mounted within the shield 14 retains the shield 14 in the ready-to-use position and inhibits distal sliding thereof. The lock flange 72 is substantially aligned with the distal end 56 of the shield 14.

After completing the medical procedure, the clinician manipulates the shield 14 forward via one-handed operation to cover the distal end 17 of the needle 16, as shown in FIG. 4. This is accomplished using the thumb or index finger to urge the actuator 62 distally along the slot 54. Alternatively, a corner of a rigid surface such as a table or counter top may be used to manipulate the shield 14. Both techniques provide relative movement between the shield 14 and the barrel 12. As the shield 14 moves forward, the narrowed interior surface 59 of the shield 14 slides along the outer surface 51 of the post 40, and along the outer surface 28 of the lock insert 26. The inner surface 61 of the shield 14 slides along the outer surface 28 of the flange 72.

Figure 5:
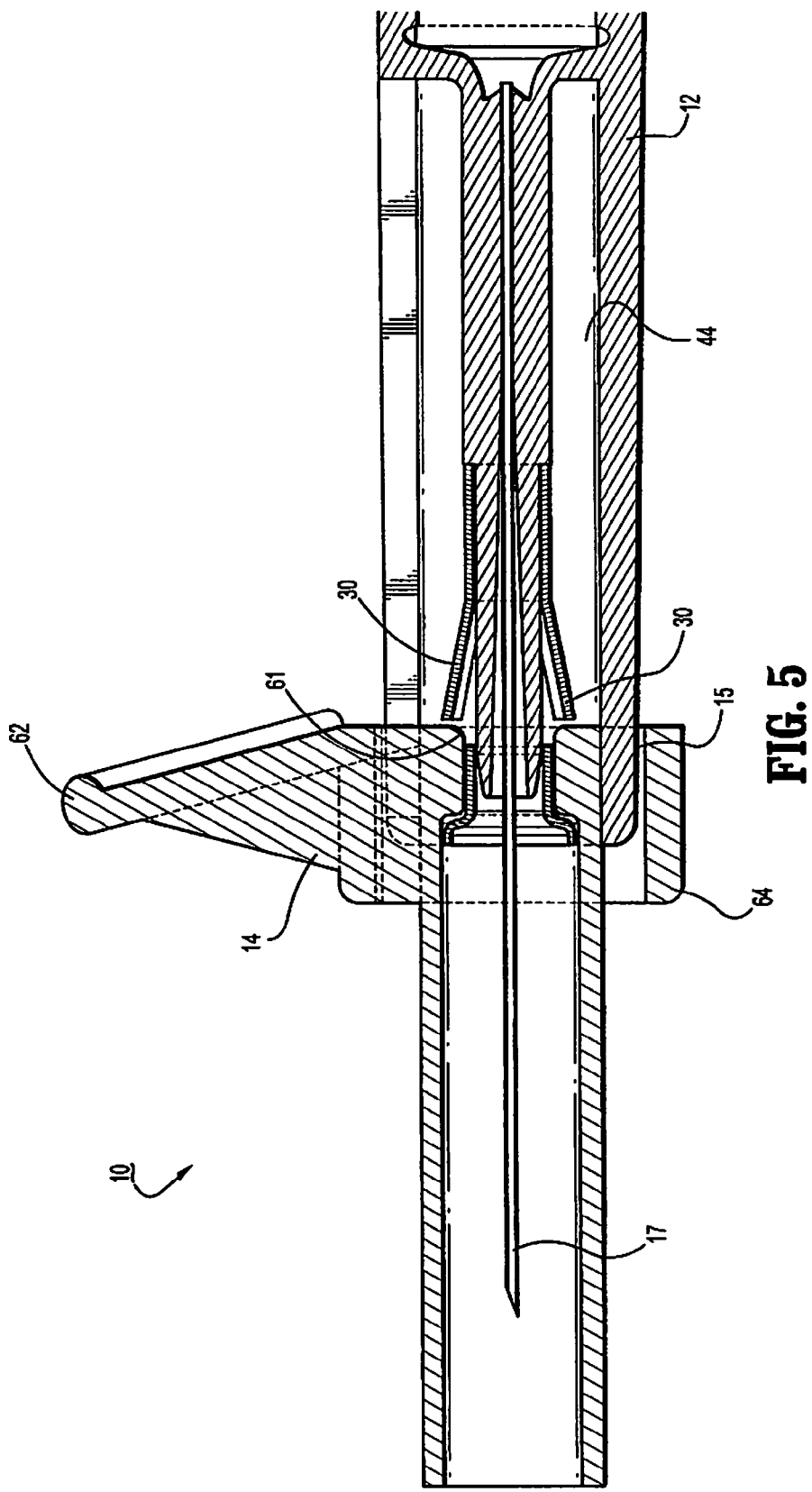
FIG. 5 is a cutaway cross-sectional side view of the distal portion of the apparatus shown in FIG. 1, in a locked position.
Figure 9:
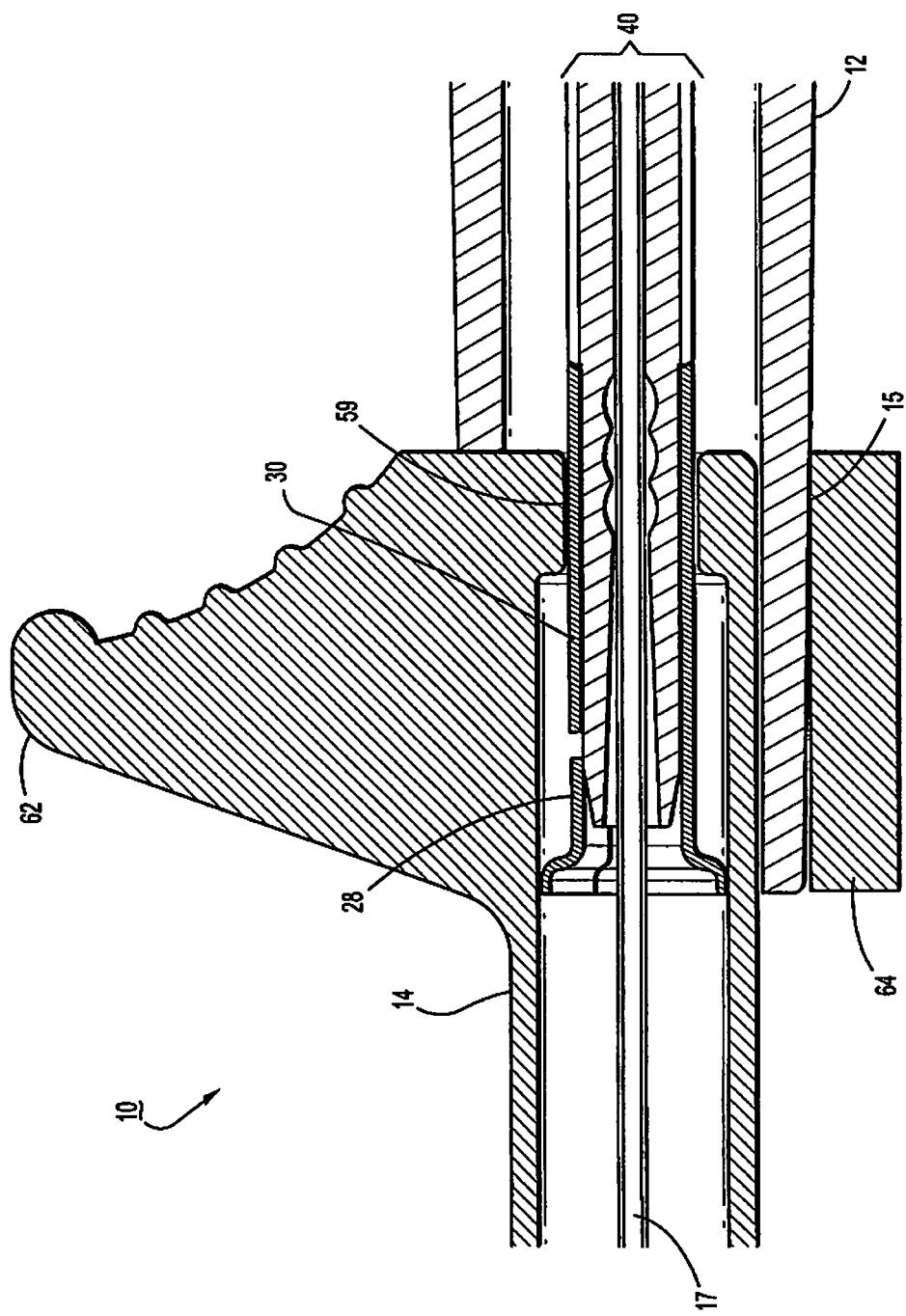
FIG. 9 is a cutaway side cross-sectional view of the distal portion of the apparatus shown in FIG. 1, in an extended position.

As the shield 14 is moved further, as shown in FIG. 9, the narrowed inner surface 59 of the shield 14 slides over the tangs 30, forcing the tangs 30 compress into substantial alignment with the lock surface 28 such that the angle A becomes substantially zero. After the narrowed surface 59 of the shield 14 slides past the compressed tang 30, as shown in FIG. 5, the tang 30 will snap back outwardly; this is because tang 30 is biased for radially outward motion. That is, the tang 30 pivots from its proximal end 30b such that the distal end 30a extends into the gap 74 to oppose any proximal (backward) movement of the shield 14. Locking of the shield 14 in this way disables the syringe 10 and inhibits re-exposure of the needle tip 17.

Figure 10:
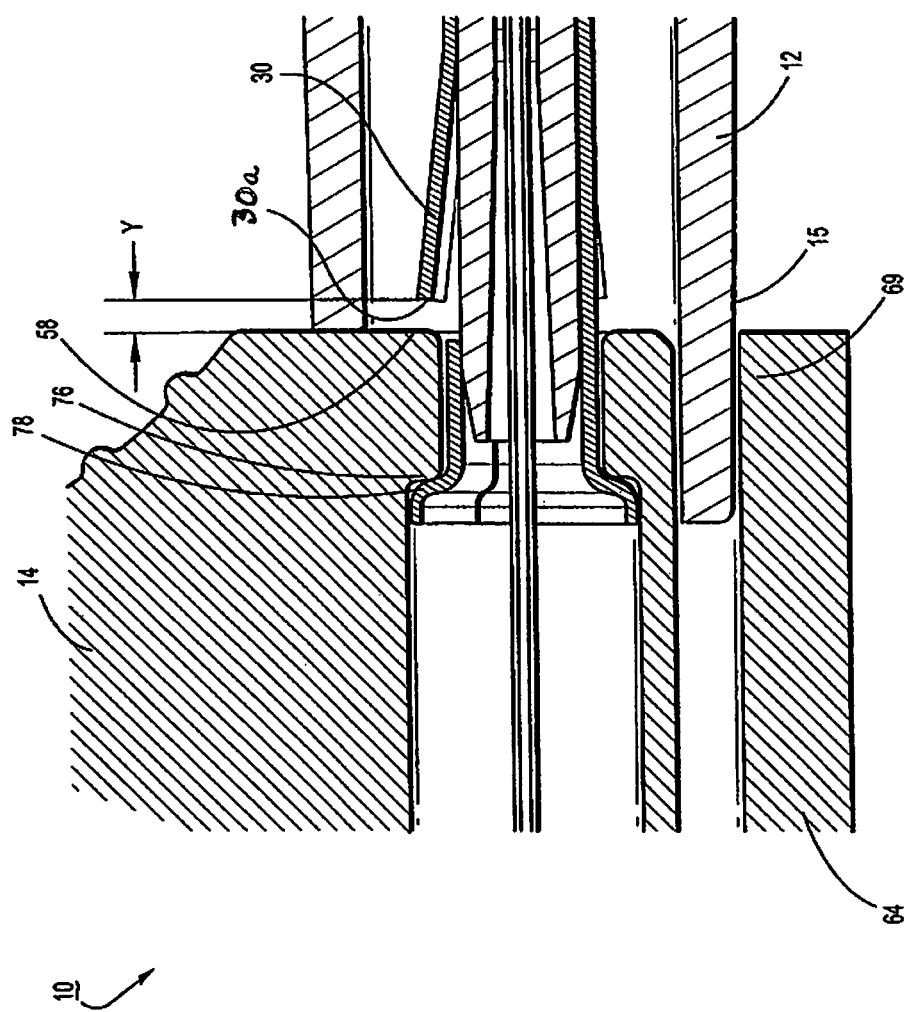
FIG. 10 is an enlarged cutaway side cross sectional view of the distal portion of the apparatus shown in FIG. 1, in a fully extended position.
Figure 11A:
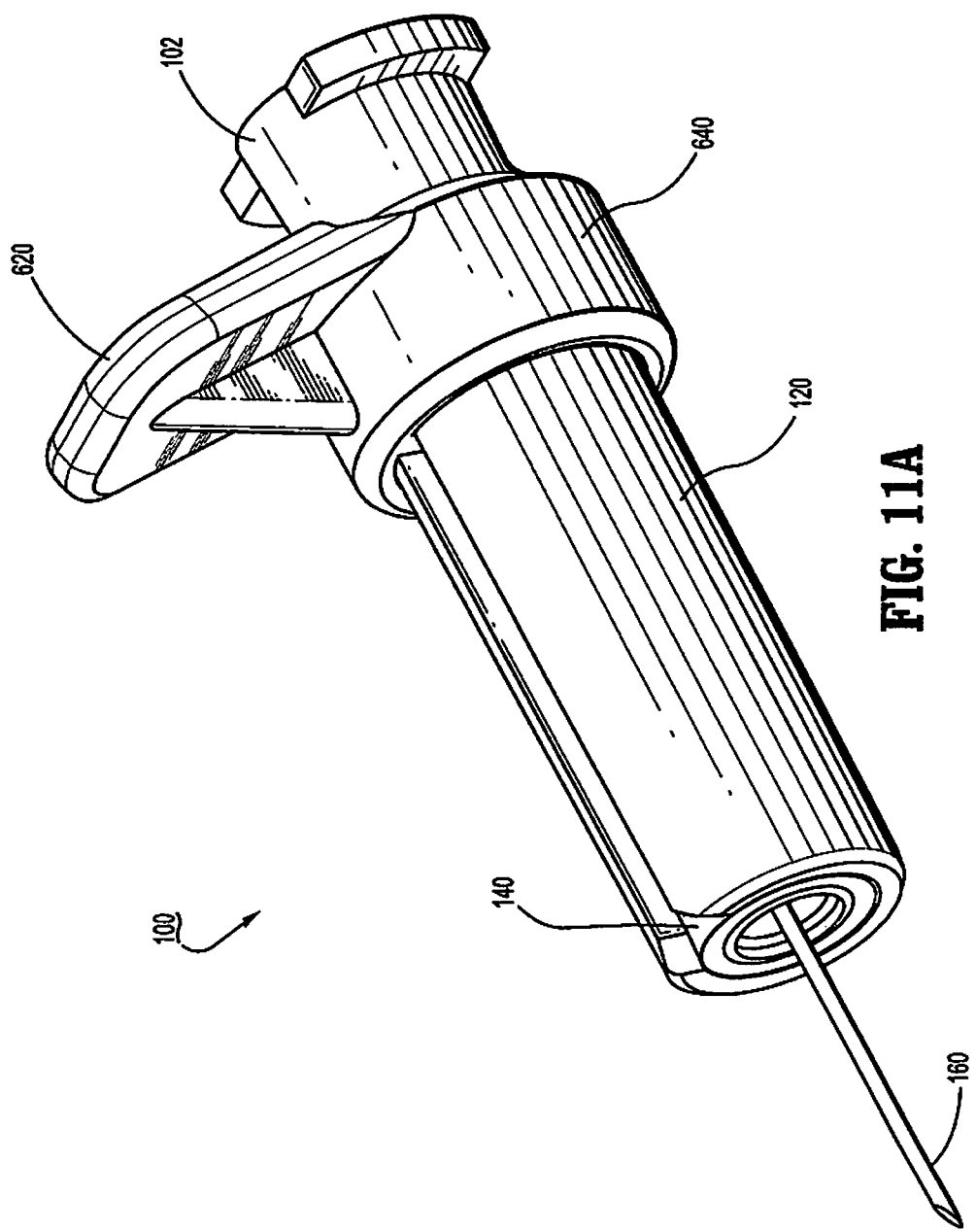
FIGS. 11A and 11B are perspective views of an alternative embodiment of the apparatus in accordance with the principles of the present disclosure.
Figure 11B:
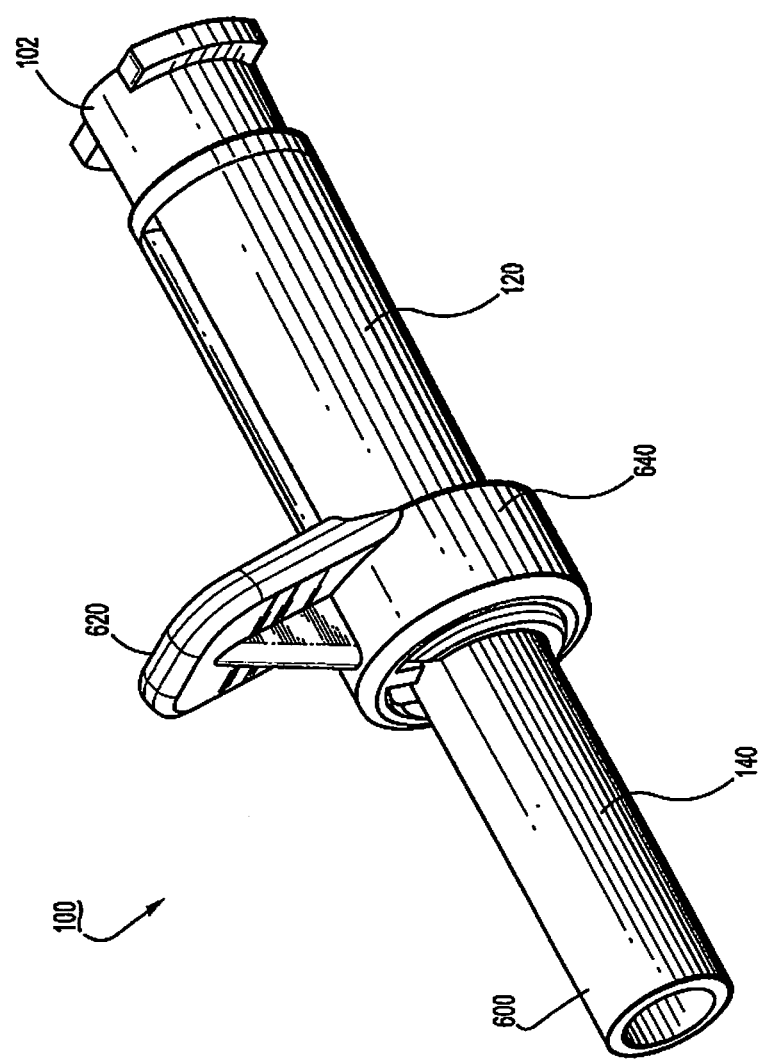
Figure 12A:
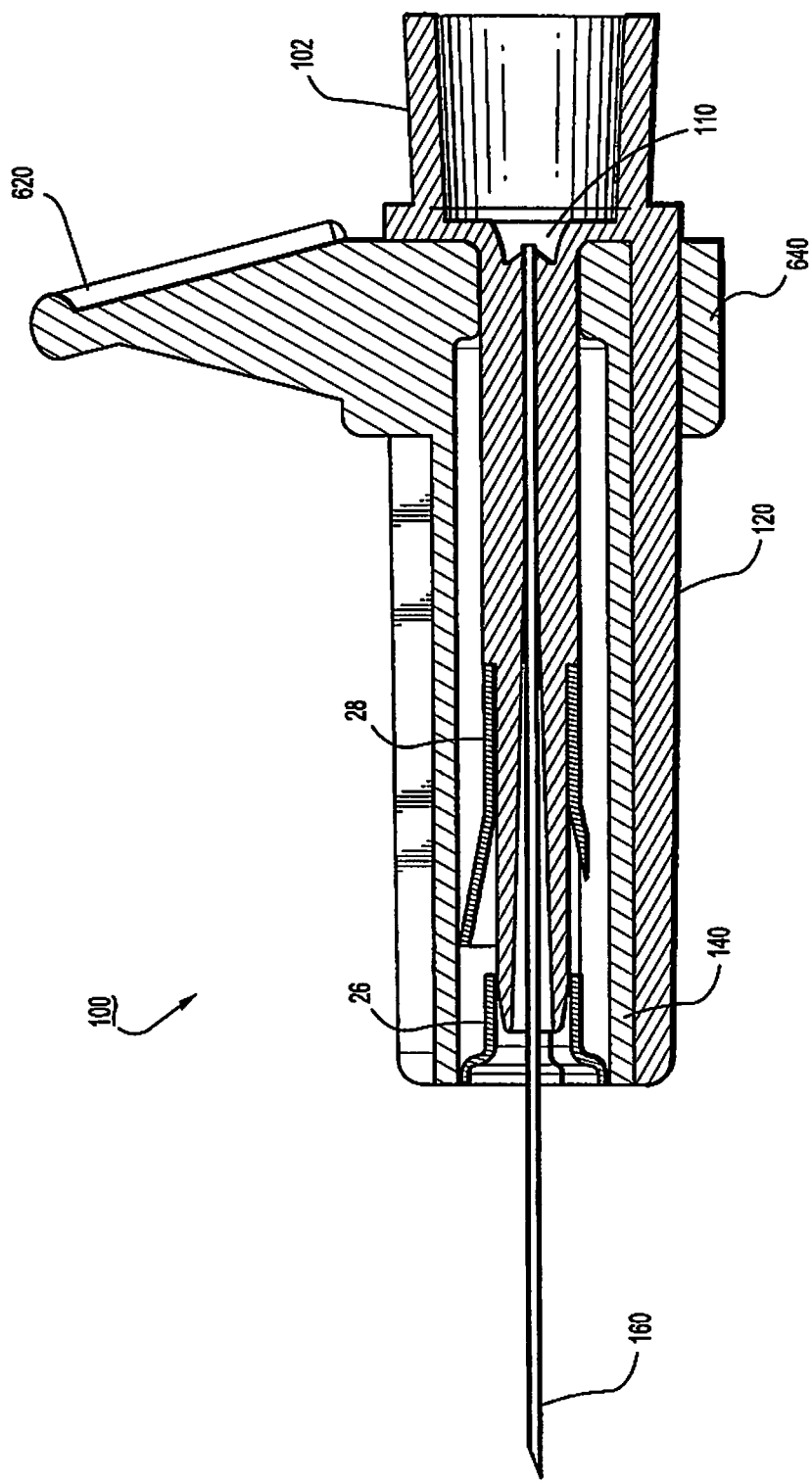
FIGS. 12A and 12B are respective cross-sectional views of the apparatus shown in FIGS. 11A and 11B.
Figure 12B:
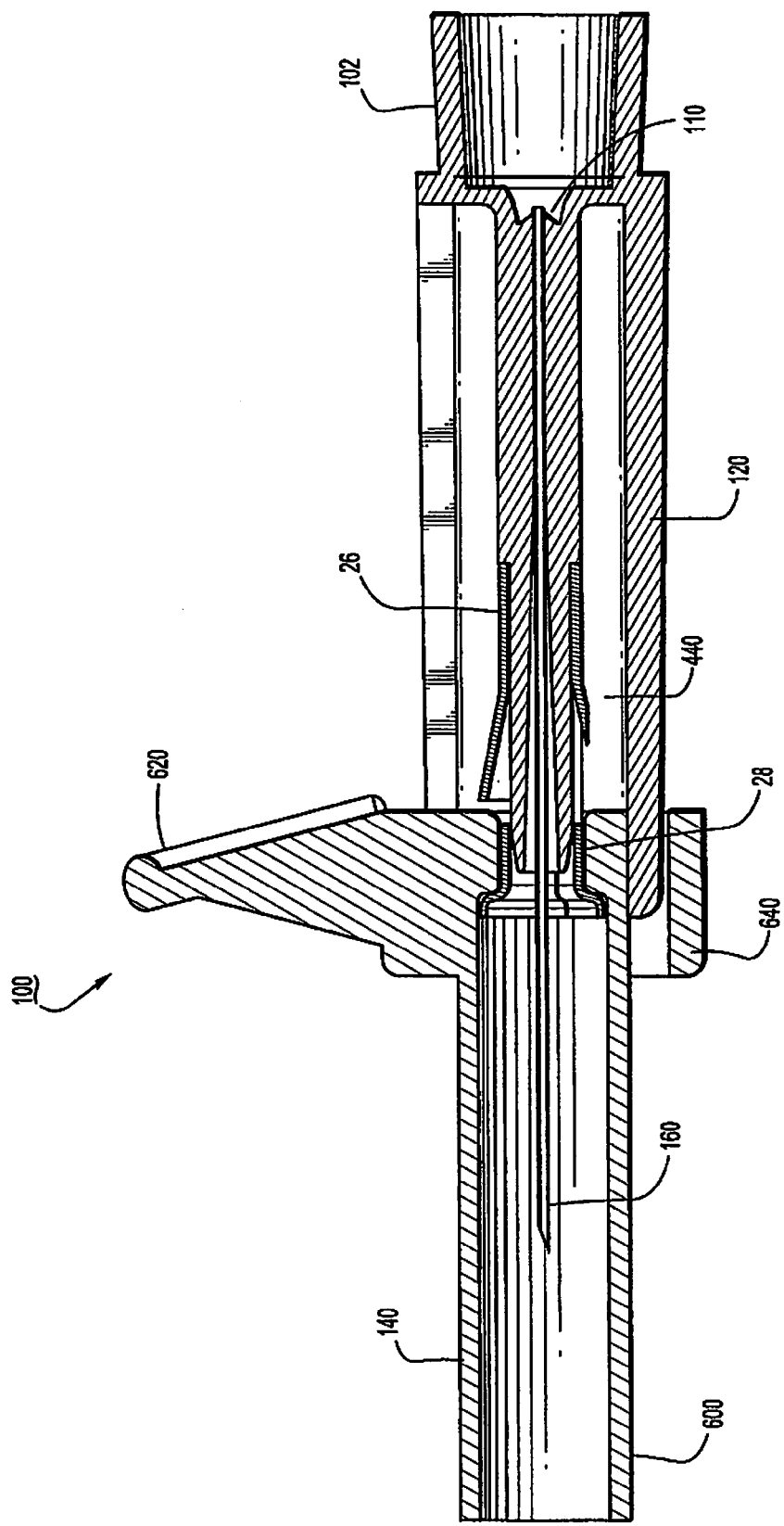

A gap Y, as shown in FIG. 10, between the distal end 30a of the tang 30 and the proximal end 58 of the shield 14 provides free play therebetween. This free play enables movement of the shield 14 to provide a tactile indicator or feedback that the shield 14 is in the fully extended position. The circumferential ridge 76 at the shield 14 interior abuts a proximal ridge 78 at the lock flange 72 to inhibit the shield 14 from traveling too far distally. The inner surface 69 of the stability ring 64 engages the outer wall 15 of the barrel 12 for added structural integrity when the shield 14 is in the fully extended position.

As discussed above, the lock insert 26 disables the safety syringe 10 by inhibiting the shield 14 from traveling proximally via tangs 30, from a fully shielded position, to re-expose needle cannula 16. The lock insert 26 defines the gap Y between a distal end 30a of the tangs 30 and the shield 14 to provide free play therebetween. This free play enables slight movement of the shield 14 to provide a tactile indicator that the shield 14 is in the fully shielded position. The lock insert 26 also inhibits the shield 14 from traveling too far distally via circumferential ridge 76 and proximal ridge 78 at the lock flange 72 that act as a forward stop. The metal lock insert 26, tangs 30, and forward stop act to inhibit movement of the shield 14 in a fully shielded position.

A desirable advantage of the combination of the gap Y between the lock insert 26 and the proximal end 58 of the shield 14 is that it minimizes lock insert 26 from kicking out through the slot 54 during a catastrophic failure of the safety syringe 10. In such a failure, safety syringe 10 would remain in its safe position. Moreover, if the safety syringe 10 were to experience a catastrophic failure, where the syringe 10 was subject to forces that would lead to breaking of the syringe 10, the syringe 10 is so designed that the proximal end of the needle cannula 16 and shield 14 would still remain in its safe position shielding the needle cannula 16.

The above-described configuration advantageously inhibits removal of the shield 14 from the syringe barrel 12. Further, mounting the shield 14 within the outer diameter of the syringe barrel 12 keeps the syringe profile extremely low. This configuration avoids impedance of administration of fluids via medical needle syringe 10, during, for example, low-angle subcutaneous injections, etc. Since the shield 14 is captured by both the inner post 40 and the outer race 46, a no-wobble, smooth extension of the shield 14 over the needle 16 is assured. The entire shield 14 is held forward of the syringe barrel 12 such that the graduations or other markings on the barrel 12 are not obscured. Other key advantages include one-hand activation of the medical needle syringe 10 and inclusion of the stability ring 62 for additional structural integrity when the shield 14 is in the fully extended or locked position.

With reference to FIGS. 11A, 11B and 12A, 12B, where like reference numerals are used to designate like elements for the sake of simplicity of explanation, there is disclosed an alternative embodiment of a safety needle apparatus or needle syringe 100 including a distally mounted standard luer fitting 102 for attachment to a syringe barrel (not shown). Similar to syringe 10, safety needle apparatus 100 includes a barrel component 120 having a needle cannula or needle 160 mounted therewith via a needle mount 110. A tubular shield 140 is mounted with the barrel 120 and is moveable from a retracted, "ready-to-use" position (FIGS. 11A and 12A) whereby the needle 160 is exposed, to an extended, "safety" position (FIGS. 11B and 12B) whereby the needle 160 is covered. A lock insert 26 is mounted with the barrel 120 such that the shield 140 is slidably movable along an outer surface 28 of the lock insert 26. A removable sheath, similar to sheath 32 (FIGS. 1 and 2), covers the needle 160 during transport and prior to use.

The shield 140 is configured for telescopic mounting within the cavity 440 (FIG. 12) of the barrel 120. The shield 140 includes a tube portion 600 configured for covering the needle 160 after as surgical procedure. An actuator 620 is disposed with the tube 600. The shield 140 includes a stability member, such as, for example, a stability ring 640 to provide additional stability during axial movement of the shield 140 with respect to the barrel 120 of the safety needle 100. The stability ring 640 adds structural integrity to keep the shield 140 firmly in place when it is locked in the fully extended position.

Figure 13A:
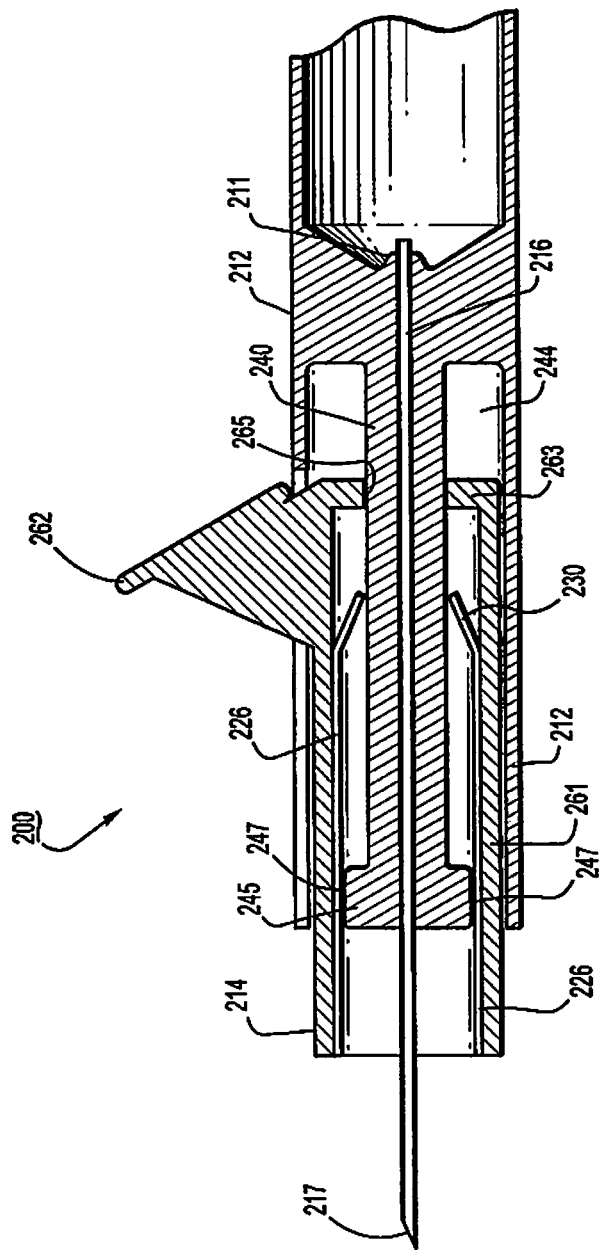
FIG. 13A is a cross-sectional side view of an alternative embodiment of the apparatus in accordance with the principles of the present disclosure, in a partially extended position.
Figure 13B:
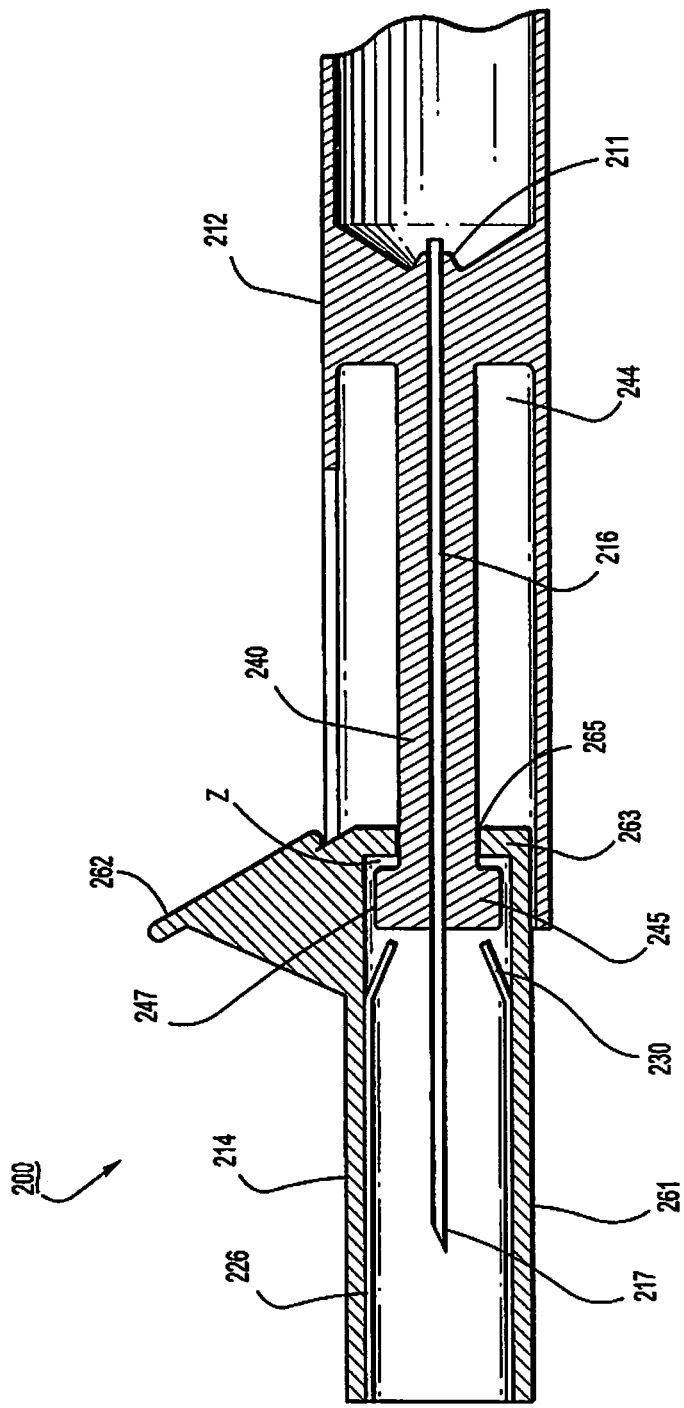
FIG. 13B is a cross-sectional side view of the apparatus shown in FIG. 13A, in an extended, locked position.

Now referring to FIGS. 13A and 13B, where like reference numerals are used to designate like elements for the sake of simplicity of explanation, there is disclosed an alternative embodiment of a safety needle apparatus or needle syringe 200 including a barrel component 212 having a needle cannula or needle 216 mounted therewith via a needle mount 211. A tubular shield 214 is mounted with the barrel 212 and is moveable from a retracted, "ready-to-use" position (not shown) and a partially extended position (FIG. 13A) whereby the needle 216 is exposed, to an extended, "safety" or "locked" position (FIG. 13B) whereby the needle 216 is covered. A lock insert 226 having at least one radially inward biased tang member 230 (two tang members 230 are shown) is mounted with the tubular shield 214 such that the lock insert 226 and tubular shield 214 are slidably movable with respect to the barrel component 212. A removable sheath, similar to sheath 32 (FIGS. 1 and 2), covers the needle 216 during transport and prior to use.

Barrel component 212 further includes a post member 240 onto which the shield 214 and lock 226 are slidably mounted. The post 240 has a distal end 245 with an extended annular surface 247. The distal end 245 has a greater diameter than that of the post 240 for engaging the tang members 230 of lock insert 226 and a proximal end wall 263 of the shield 214 (as discussed below).

The shield 214 and lock insert 226 are configured for telescopic mounting within a cavity 244 of the barrel 212. The shield 214 includes a tube portion 261 configured for covering the needle 216 after a surgical procedure. An actuator 262 is disposed with the tube portion 261 for aiding in distal movement of the shield 214. Shield 214 further includes a proximal end wall 263 having a centrally disposed through hole 265 for sliding along the post 240 of barrel 212. Proximal end wall 263 provides additional stability during axial movement of the shield 214 with respect to the barrel 212. The proximal end wall 263 adds structural integrity to keep the shield 214 firmly in place when it is locked in the fully extended position (FIG. 13B).

The operation of the safety needle apparatus 200 is similar to operation of other safety needle apparatuses (i.e. needle syringes 10 and 100) described herein. After completing the medical procedure, the clinician manipulates the shield 214 forward (i.e. distally) to cover the distal end 217 of the needle 216. As the shield 214 and lock insert 226 move forward, the interior surface of the shield 214 and tangs 230 of the lock insert 226 slide along the outer surface of the post 240. As the shield 214 is moved further, the tangs 230 are slid over the distal end 245 and extended annular surface 247 of the post 240. Consequently, the tangs 230 compress for allowing the enlarged annular surface 247 of the post 240 to pass the compressed tangs 230. The tangs 230 (being biased for radially inward motion) snap back inwardly once the shield 214 and tangs 230 are past the annular surface 247 of the post 240 (FIG. 13B). That is, the tangs 230 pivot such that the tangs 230 extend inwardly to oppose any proximal (i.e. backward) movement of the shield 214. Locking of the shield 214 in this way disables the needle apparatus 200 and inhibits re-exposure of the needle tip 217.

With reference to FIG. 13B, the proximal end wall 263 of the shield 214 abuts the distal end 245 of the post 240 to inhibit the shield 214 from traveling too far distally. Additionally, a gap Z, between the proximal end wall 263 of the shield 214 and the distal end 245 of the post 240 provides free play therebetween. This free play enables movement of the shield 214 to provide a tactile indicator or feedback that the shield 214 is in the fully extended position.

From the foregoing and with reference to the various figure drawings, those skilled in the art will appreciate that certain modifications can also be made to the present disclosure without departing from the scope of the same. For example, the first and second members can encompass varied cross-sectional shapes, for example, oval and rectangular, as long as one of the first and second members is slidably movable relative to the other. Further, as mentioned above, the safety apparatus 10 may be utilized with other medical needle applications. For example, Veress needles, Huber needles, and the like may also employ the safety apparatus 10 of the present disclosure. For illustrative purposes, the safety apparatus 10 will be described in conjunction with a Huber needle assembly designated by 400.

Figure 14:
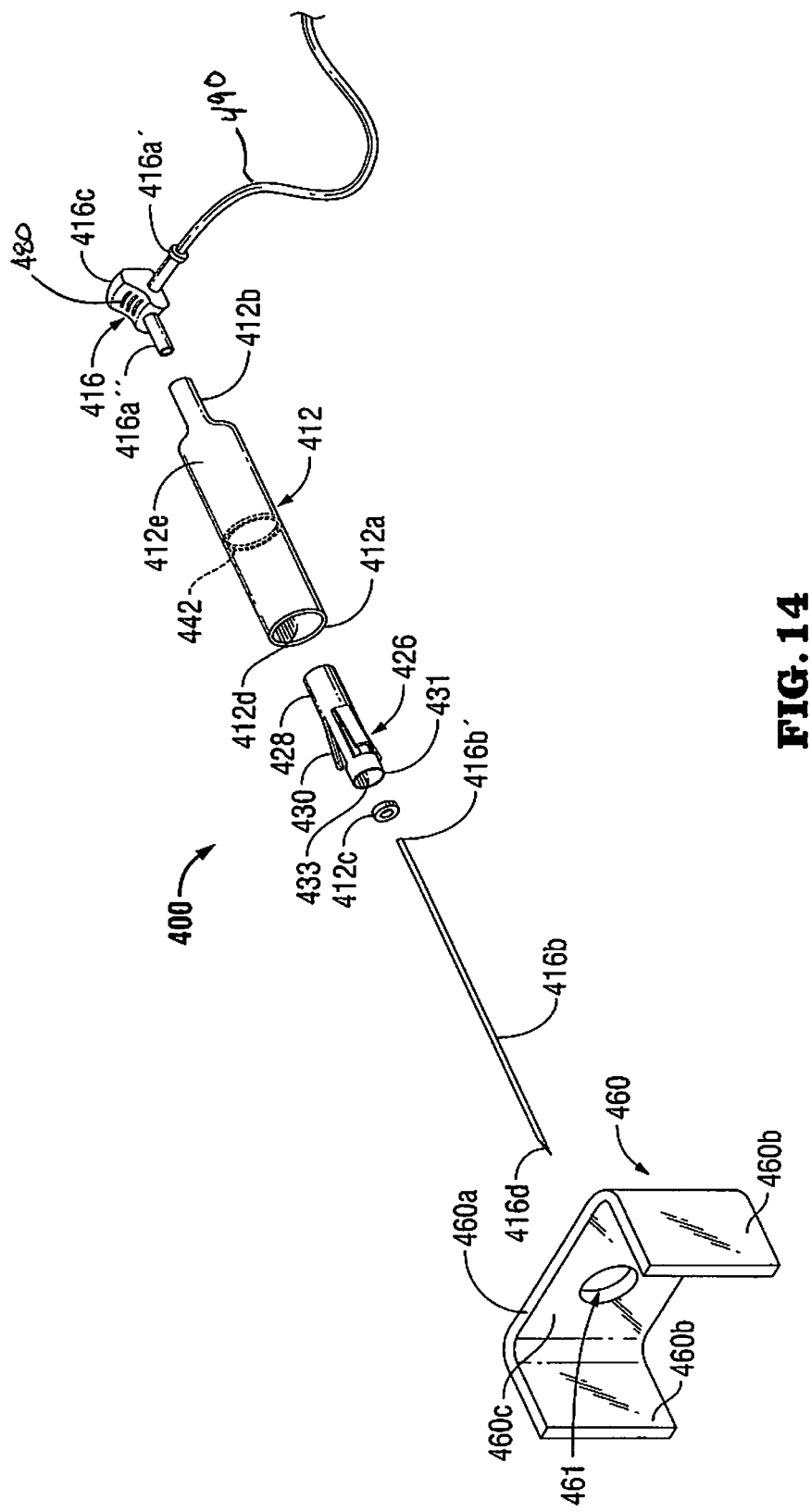
FIG. 14 is an exploded view of an alternate embodiment of a safety apparatus in accordance with the principles of the present disclosure.
Figure 15A:
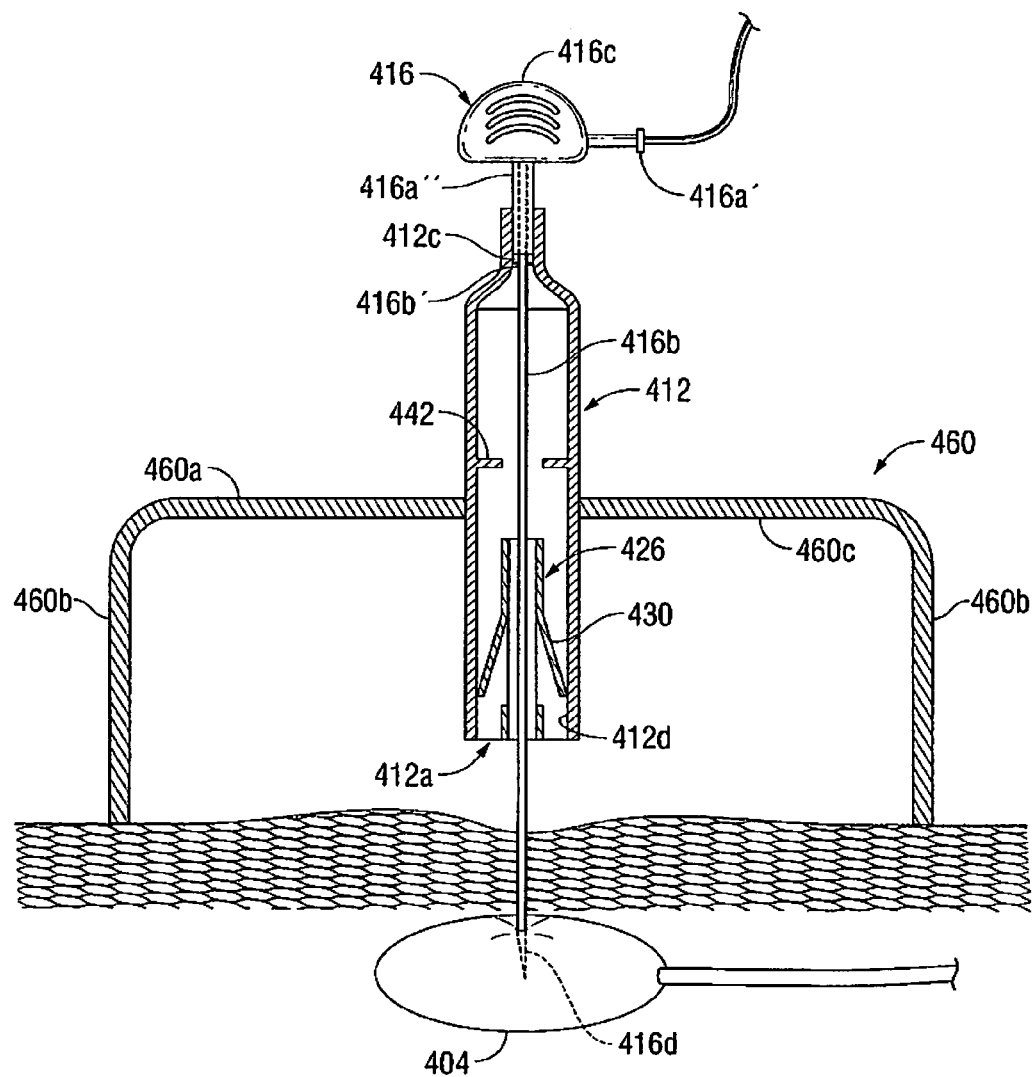
FIG. 15A is a cutaway cross-sectional of the apparatus shown in FIG. 14, with a needle in an extended position connected to a septum port in accordance with the principles of the present disclosure.
Figure 15B:
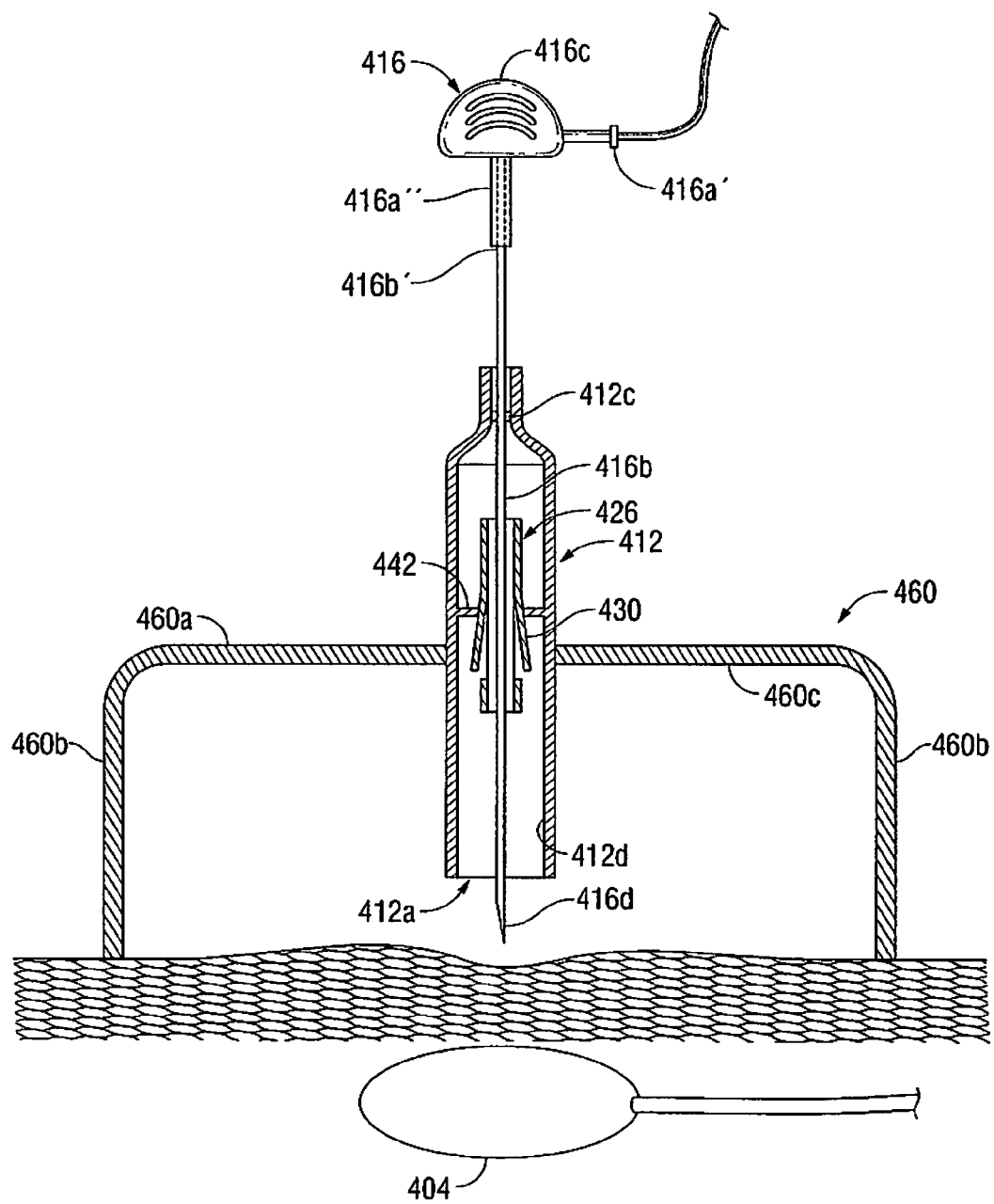
FIG. 15B is a cutaway cross-sectional of the apparatus shown in FIG. 14, with the needle in an intermediate position in accordance with the principles of the present disclosure.
Figure 15C:
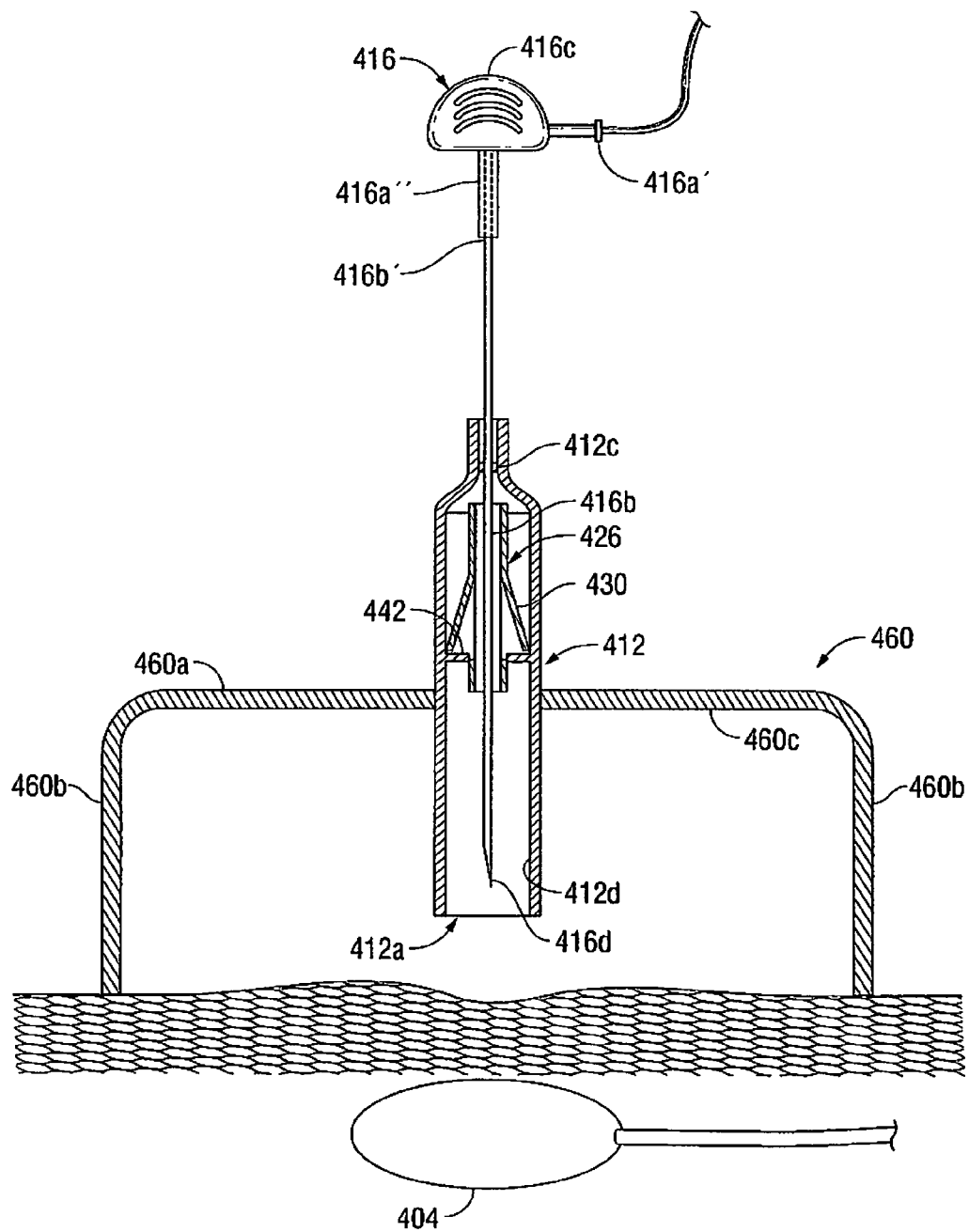
FIG. 15C is a cutaway cross-sectional of the apparatus shown in FIG. 14, with the needle in a locked position.

Referring to FIGS. 14-15C, an alternative embodiment of a safety needle apparatus 400 is disclosed. Apparatus 400 includes an annular tubular shield 412 defining a longitudinal axis, a needle assembly 416 and a needle cannula 416b. The tubular shield 412 has one or more locking members 442 mounted on an inner surface 412a of tubular shield 412. A lock insert 426 includes one or more projection members, such as for example, one or more radially inwardly biased tang members 430 (three tang members 430 are shown). The lock insert 426 is mounted to the needle cannula 416b such that the tang members 430 engage locking tabs 442 when needle cannula 416b is in a retracted position. Apparatus 400 also includes a platform 460 defining a hole 461. Hole 461 is dimensioned to receive shield 412. Shield 412 is fixedly secured to platform 460 within hole 461 using any of a variety of known fastening techniques, e.g., welding, adhesives, crimping, etc. A removable sheath, similar to sheath 32 (FIGS. 1 and 2), may be provided to cover the needle 416 during transport and prior to use.

With continued reference to FIG. 14, needle assembly 416 includes an outlet tube 416a' adapted to connect to an intravenous (I.V.) line 490. Outlet tube 416a' is in fluid communication with an inlet tube or needle mount 416a" of needle assembly 416. A finger pad 416c may be formed on needle assembly 416 to enhance gripping of needle assembly 416 during insertion and removal of needle cannula 416b into or from a patient. In one embodiment, the outlet and inlet tubes, 416a' and 416a", respectively, of needle assembly 416 may be one member having a generally "L" shape. Alternatively, the inlet and outlet tubes, of needle assembly 416 may be two separate members in fluid communication with each other.

Finger pad 416c may be configured to function similarly to conventional Huber Needle finger pads known in the art. That is, finger pad 416c allows a user to axially extend and retract needle cannula 416b as needed. In the embodiment where inlet and outlet tubes, 416a" and 416', respectively, of needle assembly 416 are two separate members, finger pad 416c may also include a channel (not shown) located on an inside surface thereof for fluidly connecting inlet and outlet tubes, 416a" and 416a', respectively. Finger pad 416c may have a generally smooth top surface, or the top surface of finger pad 416c may be textured, e.g., ribs 480, which may facilitate gripping a portion thereof.

Needle cannula 416b includes a tissue piercing distal end 416d adapted to pierce a septum of an access port 404 (FIG. 15A) implanted beneath a patient's skin, as shown in FIGS. 15A-15C. Tissue piercing distal end 416d may be configured in the same or similar manner as distal tip 17, as described above. Needle cannula 416b may be connected to finger pad 416c via inlet tube 416a" of needle assembly 416. Needle cannula 416b may be secured to inlet tube 416a" by any known fastening technique including adhesives, press fitting, crimping, and the like. Needle cannula 416b is movable in relation to shield 412 from an advanced position to a retracted position. Lock insert 426 is disposed about needle cannula 416b and is movable with needle cannula 416b from the advanced position to the retracted position.

Lock insert 426 may be attached to needle cannula 416b by any suitable means known in the art, including but not limited to adhesives, welds, crimping, press-fitting, and the like. Alternatively, lock insert 426 may be formed on needle cannula 416b at a time during the manufacture of safety needle apparatus 400. Lock insert 426 is positioned on needle cannula 416b at a distance from tissue piercing distal end 416d such that when inward biased tang members 430 are in an extended position, each tang member 430 will engage a portion of locking member 442, as shown in FIG. 15C, thus substantially preventing needle cannula 416b from moving distally toward open end 412a and preventing re-exposure of the needle tip 416d.

Lock insert 426 may be designed and configured to function in the same or similar manner as the previously described lock inserts (e.g., 26 and 260). That is, lock insert 426 may have a generally annular inner surface 433 and annular outer surface 428.

As mentioned above, lock insert 426 includes a resilient projection member, such as for example, tang 430 that extends radially outwardly in its normal configuration. One or a plurality of tangs 430 may be employed. The tangs 430 are disposed circumferentially about the outer surface 428 of the lock insert 426 intermediate distal and proximal ends 431, 437 abutting an inner surface 412d of shield 412. Tangs 430 may be configured to touch inner surface 412d of shield 412 during translation therethrough, or tang 430 may be configured to be spaced from inner surface 412d of shield 412. When needle cannula 416b is moved from its advanced position to its retracted position, tangs 430 engage locking member 442 and are compressed to pivot tang(s) 430 into substantial alignment with outer surface 428 of lock insert 426. The lock insert 426 may include other structure configured to lock the needle 416 in a retracted position, such as, stops, protuberances and the like. Operation of the lock insert 426 is described below in more detail. Although described above as having a substantially cylindrical configuration with outwardly extending tangs, it is envisioned that the lock insert may assume any of a variety of configurations which allow the needle cannula to pass over a locking member or stop surface and then spring outwardly to prevent movement of the needle cannula in the opposite direction. In this respect locking member 442 may also assume any variety of configurations which provide a stop surface for preventing advancement of the needle cannula.

The shield 412, as shown in FIG. 14, may be configured similarly or the same as the shield previously described (e.g., shield 14). Shield 412 may be defined as having a generally tubular shape extending from an open annular distal end 412a toward an open annular proximal end 412b.

Open proximal end 412b may be dimensioned to receive and/or maintain a portion of needle cannula 416b of needle assembly 416 in a substantially upright position when needle cannula 416b pierces the septum of the access port 404. Open proximal end 412b may be tapered and may include a seal member 412c. Seal member 412c seals between the outer surface of cannula 416b and an inner surface of open proximal end 412b of shield 412.

As discussed above, locking members 442 may be defined as one or more protrusions or tabs 442 having an annular shape extending inwardly from inner surface 412d of shield 412. Locking member 442 is positioned within shield 412 such that upon engagement with tangs 430 of locking insert 426, the distal tip 416d of needle cannula 416b is confined within shield 412, thus, inhibiting re-exposure of the needle tip 416d. That is, when tangs 430 of locking insert 426 pass over member 442 of shield 412, needle cannula 416b will be prevented from extending past open annular distal end 412a of shield 412.

It is contemplated that instead of employing a locking member 442 that is defined as a protrusion or tab, locking member 442 may be defined as one or more grooves or recesses 442 located on inner surface 412d of shield 412. The grooves may be disposed on inner surface 412d of shield 412 such that, when needle cannula 416b is in retracted position one or more grooves 442 will engage one or more tangs 430. It is further contemplated that the grooves may be used in place of or in combination with one or more protrusions or tabs.

Figure 16A:
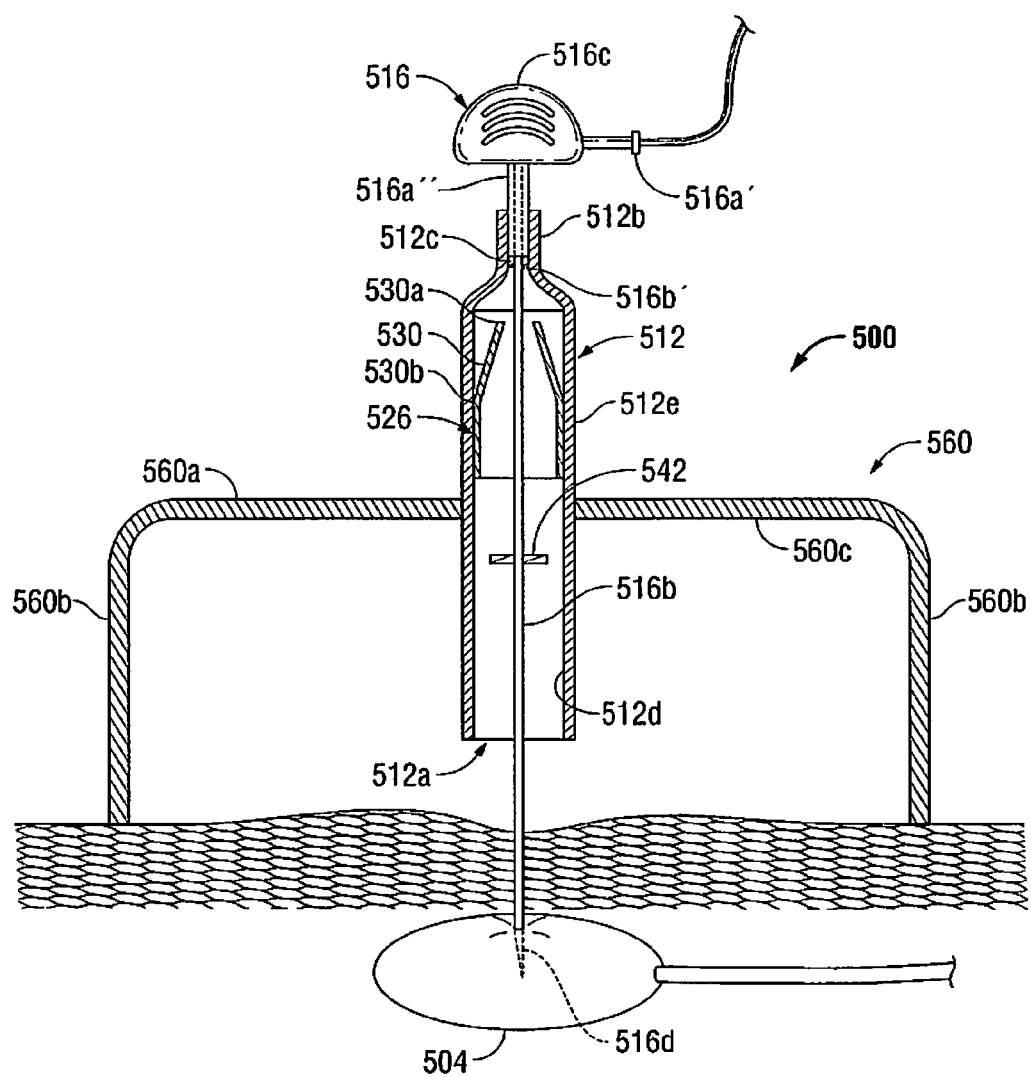
FIG. 16A is a cutaway cross-sectional of an alternate embodiment of the apparatus shown in FIG. 14, with a needle in an extended position connected to a septum port in accordance with the principles of the present disclosure.

As illustrated in FIGS. 15A and 16A, platform 460 is employed to maintain shield 412 in a substantially fixed position while needle cannula 416b is in fluid communication with the septum of access port 404. Platform 460 may be configured, dimensioned, and shaped similar to conventional platforms, employed with Huber needles, known in the art. Platform 460 includes a top surface 460a, a bottom surface 460c and base member 460b. Aperture 461 extends between top surface 460a and bottom surface 460c. Aperture 461 is provided to secure shield 412 to platform 460. Base member 460b is configured to support the apparatus on the body of a patient such that the needle cannula is substantially orthogonal to a plane defined by the top surface of platform 460.

With reference to FIGS. 15A-15C, in operation, while medication is being administered to a patient, tangs 430 extend outwardly toward inner surface 412d of shield 412. After the medication has been administered, a user may remove outlet tube 416a' of needle assembly 416 from the I.V. drip. Alternatively, a user may leave the I.V. connected to outlet tube 416a' of needle assembly 416. Prior to removing distal tip 416d of needle cannula 416b from the septum of the access port 404, needle cannula 416b will be in an extended position (FIG. 15A). A user may then apply a holding force to platform 460 with one hand and apply a retracting force to finger pad 416c with the other hand. The retracting force will retract the needle cannula 416b from the septum of access port 404. As needle cannula 416b of needle assembly 416 is retracted into shield 412, tangs 430, which are biased for radially outward motion, will move along inner surface 412d of shield 412. When tang 430 of locking insert 426 contacts a distal portion of locking member 442, tangs 430 will pivot and flex inwardly, as described above. This inward flex allows tangs 430 to pass over locking tabs 442 (FIG. 15B). After tangs 430 have past over locking tabs 442, tangs 430 will return to their normal configuration and pivot radially outward to a position located proximally of locking member 442 (FIG. 15C). As such, locking member 442 will substantially prevent advancement of needle cannula 416b. At this point of retraction, needle tip 416d is positioned within shield 412.

Figure 16B:
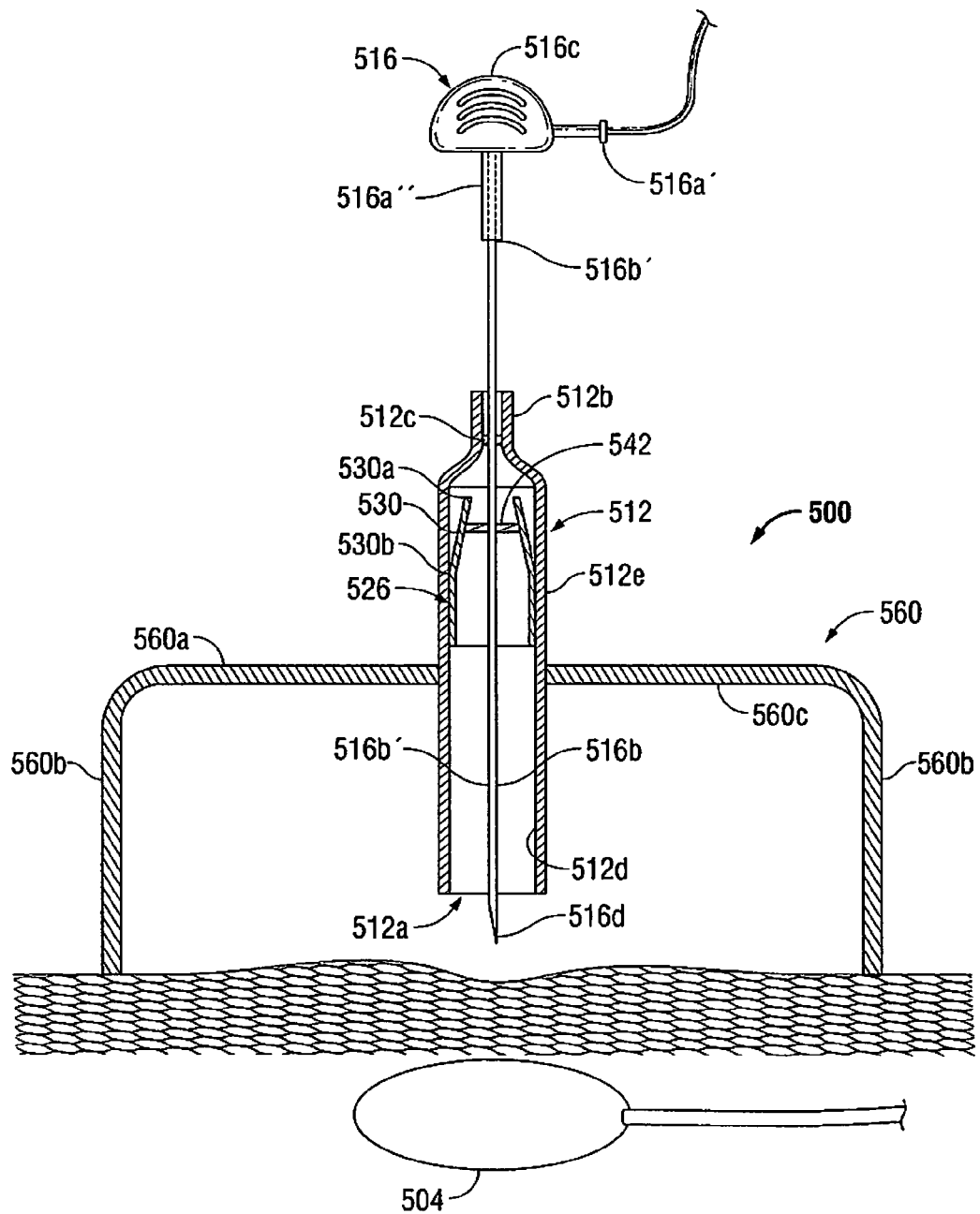
FIG. 16B is a cutaway cross-sectional of the apparatus shown in FIG. 16A, with the needle in an intermediate position in accordance with the principles of the present disclosure.
Figure 16C:
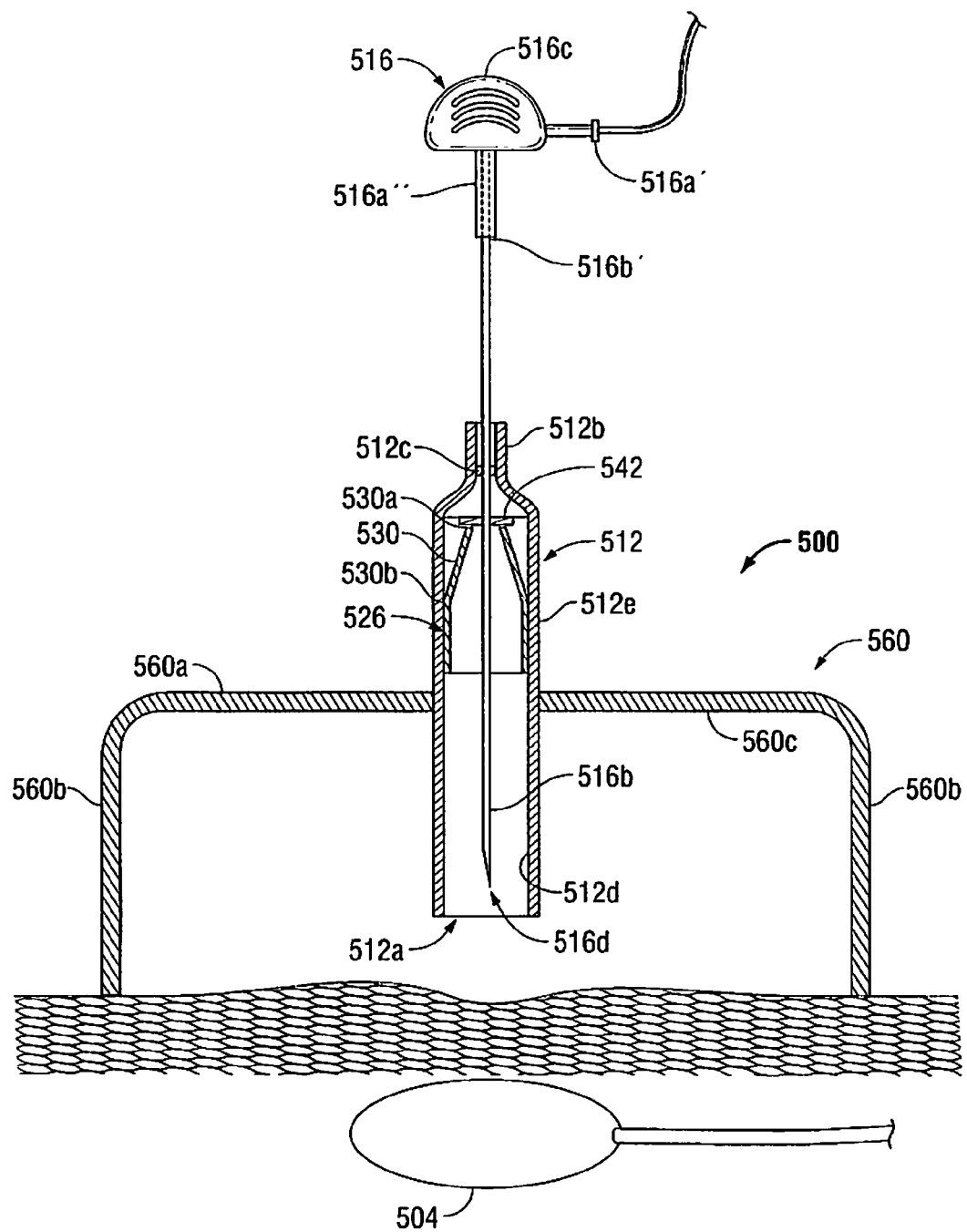
FIG. 16C is a cutaway cross-sectional of the apparatus shown in FIG. 16A, with the needle in a locked position.

With reference to FIGS. 16A-16C, there is disclosed an alternative embodiment of a safety needle apparatus 500. Safety needle apparatus 500 depicted in FIGS. 16A-16C illustrates a shield 512 and a needle assembly 516 wherein shield 512 includes a lock insert including one or more locking members 526 and needle cannula 516b of needle assembly 516 includes a locking member including one or more locking tabs or locking grooves 542.

For the purposes of brevity and to avoid obscuring the present disclosure with cumulative and unnecessary detail, only shield 512 and needle assembly 516 will be described in further detail below.

Shield 512 may be configured to operate in the same or similar manner as shield 412, as described above. Shield 512 includes open proximal tapered end 512b and distal annular end 512a. Shield 512 also includes inner and outer surfaces 512d and 512e, respectively. Inner surface 512d includes one or more locking members 526 mounted thereon.

Locking member 526 may include one or more protrusions or tangs 530 that is movable radially outward to fix the needle cannula 516b in the retracted position. Tangs 530 may be disposed circumferentially about the inner surface 512d of the shield 512 intermediate the distal and proximal ends, 512b and 512a, respectively, of shield 512. The tangs 530 are pivotable from a distal edge 530b. Tang 530 is biased for radially outward movement such that a proximal end 530a tends to extend above the inner surface 512d. When compressed, the tang 530 pivots toward alignment with the inner surface 512d. Operation of the lock member 526 is described below in more detail. It is contemplated that locking member 526 may be defined as one or more grooves or recesses, as described above.

Needle assembly 516 includes inlet and outlet tubes 516a" and 516a', respectively. Needle cannula 516b includes one or more locking tabs 542. Locking tabs 542 may be defined as having an annular shape and extending in a generally orthogonal direction from an outer surface 516b' of needle cannula 516b. Locking tabs 542 are configured and dimensioned in such a manner that upon engagement with tangs 530 of shield 512, needle cannula 516b will be prevented from moving distally toward open distal end 512a. That is, needle cannula 516b of needle assembly 516 will be prevented from extending past open annular distal end 512a of shield 512. Locking tab 542 is positioned on needle cannula 516b at a distance from tissue piercing distal end 516d such that when inward biased tang members 530 are in an extended position, each tang member 530 will engage a portion of locking tab 542, as shown in FIG. 16C, thus substantially preventing needle cannula 516b of needle assembly 516 from moving distally toward open end 512a and preventing re-exposure of the needle tip 516d.

With reference to FIGS. 16A-16C, in operation, while medication is being administered to a patient, tangs 530 extend radially inwardly from inner surface 512d of shield 512. After the medication has been administered, a user may disconnect outlet tube 516a' of needle assembly 516 from the I.V. drip. Alternatively, a user may leave the I.V. connected to outlet tube 516a' of needle assembly 516. Prior to removing distal tip 516d of needle cannula 516b from the septum of access port 504, needle cannula 516b will be in an extended position (FIG. 16A). A user may then apply a holding force to platform 560 with one hand and apply a retracting force to finger pad 516c with the other hand. The retracting force will retract the needle cannula 516b of needle assembly 516 from the septum of the access port 504. As needle cannula 516b is retracted into shield 512, locking tab 542 moves along inner surface 512d of shield 512. When locking tab 542 contacts distal edge 530b of tangs 530, tangs 530 will pivot and flex outwardly, as described above. This outward flex allows locking tabs 542 to pass over tangs 530 (FIG. 16B). After tab 542 has past over tangs 530, tangs 530 will once again pivot radially inwardly to a position to engage locking tab 542 (FIG. 16C).

It is contemplated that any number of detents, grooves, protuberances, and the like may be employed with safety needle apparatus' 400 and 500 of the present disclosure.

It is further contemplated that safety needle apparatus 400 and 500 may each include other structure to provide any of the aforementioned gap distances (e.g., gap "Y" and gap "Z").

The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A safety needle apparatus comprising:
   a needle assembly including a needle mount and a needle cannula, the needle cannula defining a lumen having a sharpened distal tip for piercing tissue, the needle mount supporting a proximal end of the needle cannula and being adapted to engage an intravenous line;
   a shield positioned about the needle cannula, the needle cannula being movable in relation to the shield from an advanced position in which the distal tip of the needle cannula extends from a distal end of the shield to a retracted position in which the distal tip of the needle cannula is positioned within the shield;
   a lock insert and a locking member, the lock insert being supported on one of the needle cannula and the shield and the locking member being supported on the other of the needle cannula and the shield; and
   a platform spaced outwardly of and fixedly supporting the shield, the platform being positioned and configured to support the safety needle apparatus on a body of a patient, the platform including a base member which is positioned about the shield and the base member extending in a generally parallel orientation with respect to the shield and configured to support the needle cannula at a substantially orthogonal orientation in relation to a plane defined by a top surface of the platform, wherein the top surface of the platform defines a hole, and the shield is fixedly secured to the platform within the hole during use of the needle cannula for piercing tissue to prevent relative longitudinal movement between the platform and the shield;
   wherein the lock insert and the locking member are configured to prevent movement of the needle cannula to the advanced position after the needle cannula has been moved to the retracted position; and
   wherein the shield is not movable relative to the platform as the needle cannula moves between the advanced position and the retracted position.

2. The safety needle apparatus of claim 1, wherein the lock insert is supported on the needle cannula and the locking member extends from an internal surface of the shield.

3. The safety needle apparatus of claim 2, wherein the lock insert includes at least one resilient projection member.

4. The safety needle apparatus of claim 3, wherein the at least one resilient projection member extends radially outwardly in its normal configuration.

5. The safety needle apparatus of claim 2, wherein the locking member includes at least one protrusion having a generally annular shape and extending inwardly from an inner surface of the shield.

6. The safety needle apparatus of claim 1, wherein the lock insert is supported . . . and the locking member extends from an outer surface of the needle cannula.

7. The safety needle apparatus of claim 6, wherein the lock insert includes at least one protrusion that is movable radially outward.

8. The safety needle apparatus of claim 6, wherein the locking member is an annular tab extending in a generally orthogonal direction from the outer surface of the needle cannula.

9. The safety needle apparatus of claim 1, wherein the base member of the platform extends downward from the top surface of the platform, the base member being substantially parallel to the needle cannula.

10. The safety needle apparatus of claim 1, wherein the platform is configured to prevent the shield from contacting the body of the patient during use of the needle cannula for piercing tissue.

11. The safety needle apparatus of claim 1, wherein the shield is permanently fixed to the platform.

\* \* \* \* \*